US008987685B2

(12) United States Patent
Fawcett et al.

(10) Patent No.: US 8,987,685 B2
(45) Date of Patent: Mar. 24, 2015

(54) OPTICAL SYSTEM FOR MULTIPLE REACTIONS

(75) Inventors: Adrian Fawcett, Carlsbad, CA (US); David Tracy, Norwalk, CT (US); Kevin Daley Simmons, San Diego, CA (US)

(73) Assignee: PCR Max Limited

(*) Notice: Subject to any disclaimer, the term of this patent is extended or adjusted under 35 U.S.C. 154(b) by 0 days.

(21) Appl. No.: 12/841,725

(22) Filed: Jul. 22, 2010

(65) Prior Publication Data

US 2011/0057117 A1    Mar. 10, 2011

Related U.S. Application Data

(60) Provisional application No. 61/240,951, filed on Sep. 9, 2009, provisional application No. 61/296,847, filed on Jan. 20, 2010.

(51) Int. Cl.
*G01J 1/58* (2006.01)
*G01N 21/64* (2006.01)
*B01L 7/00* (2006.01)

(52) U.S. Cl.
CPC ............. *G01N 21/6452* (2013.01); *B01L 7/52* (2013.01); *B01L 2300/046* (2013.01); *B01L 2300/0829* (2013.01); *B01L 2300/1805* (2013.01); *G01N 2021/6421* (2013.01); *G01N 2201/0626* (2013.01); *G01N 2201/0627* (2013.01); *G01N 2201/0636* (2013.01)
USPC .................. 250/458.1; 250/459.1; 250/461.1

(58) Field of Classification Search
USPC ................................ 250/458.1, 459.1, 461.1
See application file for complete search history.

(56) References Cited

U.S. PATENT DOCUMENTS

| | | | |
|---|---|---|---|
| 2,962,268 | A | 11/1960 | Soltermann |
| 4,683,202 | A | 7/1987 | Mullis |
| 4,824,329 | A | 4/1989 | Yamamoto et al. |
| 5,079,352 | A | 1/1992 | Gelfand et al. |
| 5,210,015 | A | 5/1993 | Gelfand et al. |
| 5,310,652 | A | 5/1994 | Gelfand et al. |
| 5,314,809 | A | 5/1994 | Erlich et al. |

(Continued)

FOREIGN PATENT DOCUMENTS

| | | |
|---|---|---|
| EP | 0363143 | 4/1990 |
| EP | 0512334 | 11/1992 |

(Continued)

OTHER PUBLICATIONS

Vishnoi, N. "Gradient Palm-Cycler TM From Corbett Life Science," Feb. 23, 2007, available at: http://www.biocompare.com/Articles/ProductReview/787/Gradient-Palm-Cycler-From-Corbett-Life-Science.html (accessed Apr. 27, 2011).

(Continued)

*Primary Examiner* — Christine Sung
(74) *Attorney, Agent, or Firm* — McCarter & English, LLP; Maria Laccotripe Zacharakis

(57) ABSTRACT

Optical systems, and corresponding methods, for multiple reactions are provided. The optical systems are in a fixed position relative to a thermal assembly and include at least one array of excitation sources (e.g., light emitting diodes (LEDs)) configured to output excitation energy along an excitation optical path. In addition, a detector configured to receive emission energy along a detection optical path in the same plane as the excitation optical path is also provided.

28 Claims, 25 Drawing Sheets

(56) References Cited

U.S. PATENT DOCUMENTS

| | | | |
|---|---|---|---|
| 5,322,770 | A | 6/1994 | Gelfand |
| 5,323,008 | A | 6/1994 | Studholme et al. |
| 5,401,465 | A | 3/1995 | Smethers et al. |
| 5,407,800 | A | 4/1995 | Gelfand et al. |
| 5,431,339 | A | 7/1995 | Yoda |
| 5,455,175 | A | 10/1995 | Wittwer et al. |
| 5,475,610 | A | 12/1995 | Atwood et al. |
| 5,487,972 | A | 1/1996 | Gelfand et al. |
| 5,508,197 | A | 4/1996 | Hansen et al. |
| 5,538,848 | A | 7/1996 | Livak et al. |
| 5,552,580 | A | 9/1996 | Pfost et al. |
| 5,602,756 | A | 2/1997 | Atwood et al. |
| 5,618,711 | A | 4/1997 | Gelfand et al. |
| 5,643,535 | A | 7/1997 | Smethers et al. |
| 5,656,493 | A | 8/1997 | Mullis et al. |
| 5,677,152 | A | 10/1997 | Birch et al. |
| 5,716,583 | A | 2/1998 | Smethers et al. |
| 5,773,258 | A | 6/1998 | Birch et al. |
| 5,789,224 | A | 8/1998 | Gelfand et al. |
| 5,795,547 | A | 8/1998 | Moser et al. |
| 5,871,908 | A | 2/1999 | Henco et al. |
| 5,928,907 | A | 7/1999 | Woudenberg et al. |
| 5,935,522 | A | 8/1999 | Swerdlow et al. |
| 5,972,716 | A | 10/1999 | Ragusa et al. |
| 5,994,056 | A | 11/1999 | Higuchi |
| 6,015,674 | A | 1/2000 | Woudenberg et al. |
| 6,127,155 | A | 10/2000 | Gelfand et al. |
| 6,140,613 | A | 10/2000 | Tsuno |
| 6,144,448 | A | 11/2000 | Mitoma |
| 6,153,426 | A | 11/2000 | Heimberg |
| 6,171,785 | B1 | 1/2001 | Higuchi |
| 6,174,670 | B1 | 1/2001 | Wittwer et al. |
| 6,232,079 | B1 | 5/2001 | Wittwer et al. |
| 6,245,514 | B1 | 6/2001 | Wittwer et al. |
| 6,303,305 | B1 | 10/2001 | Wittwer et al. |
| 6,472,186 | B1 | 10/2002 | Quintanar et al. |
| 6,503,720 | B2 | 1/2003 | Wittwer et al. |
| 6,533,255 | B1 | 3/2003 | Mitsuhashi et al. |
| 6,555,792 | B1 | 4/2003 | Elsener et al. |
| 6,569,627 | B2 | 5/2003 | Wittwer et al. |
| 6,638,761 | B2 | 10/2003 | Shin et al. |
| 6,665,186 | B1 | 12/2003 | Calmidi et al. |
| 6,677,151 | B2 | 1/2004 | Sandell |
| 6,691,041 | B2 | 2/2004 | Sagner et al. |
| 6,703,236 | B2 | 3/2004 | Atwood |
| 6,708,501 | B1 | 3/2004 | Ghoshal et al. |
| 6,730,501 | B2 | 5/2004 | Eyre |
| 6,744,502 | B2 | 6/2004 | Hoff et al. |
| 6,746,864 | B1 | 6/2004 | McNeil et al. |
| 6,787,338 | B2 | 9/2004 | Wittwer et al. |
| 6,800,452 | B1 | 10/2004 | McNeil et al. |
| 6,814,934 | B1 | 11/2004 | Higuchi |
| 6,818,437 | B1 | 11/2004 | Gambini et al. |
| 6,825,927 | B2 | 11/2004 | Goldman et al. |
| 6,852,986 | B1 * | 2/2005 | Lee et al. ............... 250/458.1 |
| 6,873,417 | B2 | 3/2005 | Bahatt et al. |
| 6,875,604 | B2 | 4/2005 | Shin et al. |
| 6,982,166 | B2 | 1/2006 | Sandell |
| 7,008,789 | B2 | 3/2006 | Gambini et al. |
| 7,015,484 | B2 * | 3/2006 | Gillispie et al. ......... 250/458.1 |
| 7,081,226 | B1 | 7/2006 | Wittwer et al. |
| 7,109,495 | B2 | 9/2006 | Lee et al. |
| 7,122,799 | B2 | 10/2006 | Hsieh et al. |
| 7,131,286 | B2 | 11/2006 | Ghoshal et al. |
| 7,141,370 | B2 | 11/2006 | Hassibi et al. |
| 7,148,043 | B2 | 12/2006 | Kordunsky et al. |
| 7,169,355 | B1 | 1/2007 | Shin et al. |
| 7,183,103 | B2 | 2/2007 | Gambini et al. |
| RE39,566 | E | 4/2007 | Elsener et al. |
| 7,238,321 | B2 | 7/2007 | Wittwer et al. |
| 7,238,517 | B2 | 7/2007 | Atwood et al. |
| 7,273,749 | B1 | 9/2007 | Wittwer et al. |
| 7,289,217 | B2 | 10/2007 | Boege et al. |
| 7,315,376 | B2 | 1/2008 | Bickmore, Jr. et al. |
| 7,373,253 | B2 | 5/2008 | Eyre |
| 7,387,887 | B2 | 6/2008 | Wittwer et al. |
| 7,387,891 | B2 | 6/2008 | Boege et al. |
| 7,407,798 | B2 | 8/2008 | Oldham et al. |
| 7,410,793 | B2 | 8/2008 | Boege et al. |
| 7,414,724 | B2 | 8/2008 | Eckert et al. |
| 7,427,380 | B2 | 9/2008 | McNeil et al. |
| 7,504,241 | B2 | 3/2009 | Atwood et al. |
| 7,537,377 | B2 | 5/2009 | Atwood et al. |
| 7,560,273 | B2 | 7/2009 | Sandell |
| 7,577,064 | B2 | 8/2009 | Marsche et al. |
| 7,582,429 | B2 | 9/2009 | Wittwer et al. |
| 7,663,750 | B2 | 2/2010 | Bahatt et al. |
| 7,666,664 | B2 | 2/2010 | Sarofim et al. |
| 7,670,832 | B2 | 3/2010 | Wittwer et al. |
| 7,808,636 | B2 * | 10/2010 | Schulkin et al. ............... 356/365 |
| 2001/0046050 | A1 | 11/2001 | Hoyt |
| 2002/0006619 | A1 | 1/2002 | Cohen et al. |
| 2002/0086417 | A1 | 7/2002 | Chen |
| 2002/0164114 | A1 | 11/2002 | Golub et al. |
| 2002/0192755 | A1 | 12/2002 | Francis et al. |
| 2003/0138244 | A1 | 7/2003 | Long et al. |
| 2003/0150957 | A1 | 8/2003 | Thomas |
| 2003/0157498 | A1 | 8/2003 | Eyre et al. |
| 2003/0157721 | A1 | 8/2003 | Turner |
| 2003/0165867 | A1 | 9/2003 | Eyre et al. |
| 2003/0224434 | A1 | 12/2003 | Wittwer et al. |
| 2003/0230728 | A1 | 12/2003 | Dai et al. |
| 2003/0233008 | A1 | 12/2003 | Ooms et al. |
| 2004/0014202 | A1 | 1/2004 | King et al. |
| 2004/0023229 | A1 | 2/2004 | Rigler |
| 2004/0025210 | P1 | 2/2004 | Beineke |
| 2004/0142459 | A1 | 7/2004 | Sandell |
| 2004/0178357 | A1 | 9/2004 | King |
| 2004/0214315 | A1 | 10/2004 | Saluz et al. |
| 2004/0224317 | A1 | 11/2004 | Kordunsky et al. |
| 2004/0241048 | A1 | 12/2004 | Shin et al. |
| 2005/0133724 | A1 | 6/2005 | Hsieh et al. |
| 2005/0136448 | A1 | 6/2005 | Hartel et al. |
| 2005/0221367 | A1 | 10/2005 | Tran |
| 2005/0226782 | A1 | 10/2005 | Reed et al. |
| 2005/0279949 | A1 | 12/2005 | Oldham et al. |
| 2006/0006344 | A1 | 1/2006 | Boege |
| 2006/0008897 | A1 | 1/2006 | Sandell |
| 2006/0019253 | A1 | 1/2006 | Wittwer et al. |
| 2006/0029965 | A1 | 2/2006 | Wittwer |
| 2006/0048518 | A1 | 3/2006 | Bell |
| 2006/0065652 | A1 | 3/2006 | Brown |
| 2006/0105433 | A1 | 5/2006 | Bickmore et al. |
| 2006/0128009 | A1 | 6/2006 | Cerrone |
| 2006/0157223 | A1 | 7/2006 | Gelorme et al. |
| 2006/0199259 | A1 | 9/2006 | Gambini |
| 2006/0269641 | A1 | 11/2006 | Atwood et al. |
| 2006/0289786 | A1 | 12/2006 | Taylor et al. |
| 2007/0105212 | A1 | 5/2007 | Oldham |
| 2007/0114444 | A1 | 5/2007 | Reid et al. |
| 2007/0148761 | A1 | 6/2007 | Cerrone |
| 2007/0154939 | A1 | 7/2007 | Cerrone |
| 2007/0238161 | A1 | 10/2007 | Cerrone |
| 2008/0038163 | A1 | 2/2008 | Boege et al. |
| 2008/0050781 | A1 | 2/2008 | Oldham et al. |
| 2008/0116382 | A1 | 5/2008 | Eckert et al. |
| 2008/0124722 | A1 | 5/2008 | Dromaretsky et al. |
| 2008/0194014 | A1 | 8/2008 | Young et al. |
| 2008/0277595 | A1 * | 11/2008 | Lundquist et al. ......... 250/458.1 |
| 2008/0299651 | A1 | 12/2008 | Atwood |
| 2009/0009767 | A1 | 1/2009 | Boege |
| 2009/0141272 | A1 | 6/2009 | Oldham |
| 2009/0155765 | A1 | 6/2009 | Atwood |
| 2009/0176282 | A1 | 7/2009 | Sandell |
| 2010/0019157 | A1 | 1/2010 | Furlan |
| 2010/0028988 | A1 * | 2/2010 | Chu et al. ............... 435/288.4 |

FOREIGN PATENT DOCUMENTS

| | | |
|---|---|---|
| EP | 775298 | 2/1996 |
| EP | 0236069 | 5/1997 |
| EP | 1335028 A2 | 8/2003 |
| EP | 1335028 A3 | 8/2003 |
| EP | 1335028 B1 | 8/2003 |

(56) References Cited

FOREIGN PATENT DOCUMENTS

| | | |
|---|---|---|
| EP | 1470253 | 8/2003 |
| EP | 725929 | 11/2003 |
| EP | 1157744 | 3/2004 |
| EP | 1880175 | 11/2006 |
| EP | 1943655 | 3/2007 |
| EP | 1228357 | 5/2008 |
| JP | 07185363 | 7/1995 |
| JP | 2005-117987 | 5/2005 |
| WO | WO 2004/105947 | 12/2004 |
| WO | WO 2005/051065 A2 | 6/2005 |
| WO | WO 2005/051065 A3 | 10/2005 |
| WO | WO 2005/096320 A2 | 10/2005 |
| WO | WO 2006-002226 | 1/2006 |
| WO | WO 2005/096320 A3 | 4/2006 |
| WO | WO 2007/150043 | 12/2007 |
| WO | WO 2008/024080 | 2/2008 |
| WO | WO 2008/070198 | 6/2008 |
| WO | WO 2008-070198 | 6/2008 |
| WO | WO 2008/091425 | 7/2008 |
| WO | WO 2009/098624 | 8/2009 |

OTHER PUBLICATIONS

Heid et al., "Real time quantitative PCR," Genome Research, 1996, vol. 6, pp. 986-994.

Morrison et al., "Solution-phase detection of polynucleotides using interacting fluorescent labels and competitive hybridization," Analytical Biochem, 1989, vol. 183, pp. 231-244.

Schoder et al., "Novel approach for assessing performance of PCR cyclers used for diagnostic testing," J. Clin. Microbiol., 2005, Vo. 43, No. 6, pp. 2724-2728.

Voight et al., "A review of ammonia-mediated buoyancy in squids (Cephalopoda: Teuthoidea)," Mar. Fresh. Behav. Physiol., 1994, vol. 25, pp. 193-203.

Chemicool web page for mercury [online] [retrieved on Jan. 25, 2001] retrieved from http://www.chemicool.com/elements/mercury.html, 5 pages.

Department of Homeland Security—Guide for the selection of biological agent detection equipment for emergency first responders, Guide 101-04, Mar. 2005, vol. II, 324 pages.

European Search Report dated Sep. 15, 2010, European Application No. EP 10007637.

\* cited by examiner

1702

OPTICAL SYSTEM FOR MULTIPLE REACTIONS

CROSS-REFERENCE TO RELATED APPLICATIONS

This application claims priority to U.S. Provisional Application No. 61/240,951 filed on Sep. 9, 2009 and U.S. Provisional Application No. 61/296,847 filed on Jan. 20, 2010, each of which is hereby incorporated by reference in its entirety.

BACKGROUND

1. Field of the Invention

This application relates to thermocylers. More specifically, this application relates to systems and methods for detecting amplification of molecules using the polymerase chain reaction and other reactions.

2. Description of the Related Art

The advent of Polymerase Chain Reaction (PCR) in 1983 has revolutionized molecular biology through vastly extending the capability to identify, manipulate, and reproduce genetic materials such as DNA. Now, PCR is routinely practiced in medical and biological research laboratories for a variety of tasks, such as the detection of hereditary diseases, the identification of genetic fingerprints, the diagnosis of infectious diseases, the cloning of genes, paternity testing, and DNA computing. The method has been automated through the use of thermal stable DNA polymerases and machines capable of heating and cooling genetic samples rapidly, commonly known as thermal cyclers.

The optical measurements useful for interrogating these reactions can involve the measurement of fluorescence. To measure fluorescence, excitation light is directed at the samples in the sample vessels, and light emitted from the fluorophores in the samples is detected. It is often desirable that the transfer of light from the light source to the wells be carried out effectively and efficiently. Optical systems for directing light to sample plates is known, for example, as described in U.S. Pat. Nos. 6,942,837, 7,369,227, 6,852,986, and 7,410,793. While optical systems for directing light to sample vessels in plates and detecting light from the sample vessels have been developed in the art, there remains a need for optical systems which can do so more effectively and efficiently.

SUMMARY

The systems and methods described in the claims each have several features, no single one of which is solely responsible for its desirable attributes. Without limiting the scope of this invention, certain features will now be briefly discussed.

One aspect of the disclosure is a system that includes a thermal assembly configured to hold a sample plate. The system also includes an optical assembly in a fixed position relative to the thermal assembly. The optical assembly includes at least one array of excitation sources configured to emit excitation energy along an excitation optical path, and a detector configured to receive emission energy along a detection optical path. The excitation optical path and the detection optical path are in the same plane.

In certain implementations, the system further includes one or more a multifunction mirror; an excitation source assembly comprising an array of excitation sources; an emission filter slide; a detection lens assembly; a set of excitation optics; or a control assembly. In some of these implementations, the system includes a multifunction mirror, two excitation source assemblies, two sets of excitation optics and a detector. According to various implementations, in the excitation optical path, an excitation source assembly and a set of excitation optics is positioned on one side of the multifunction mirror and another excitation source assembly and another set of excitation optics is positioned on the other side of the multifunction mirror. Additionally, in a number of implementations, the excitation source assembly is positioned in the excitation optical path and wherein the excitation source assembly includes individual light emitting diodes (LEDs) corresponding to individual wells on the sample plate. In some implementations, the excitation source assembly further includes an LED array comprising the LEDs. In accordance with certain implementations, the excitation source assembly further includes a lenslet array including individual lenslets corresponding to individual LEDs in the LED array.

In certain implementations, the multifunction mirror is positioned in the excitation optical path to direct excitation energy from individual LEDs to the corresponding wells of the sample plate and is further positioned in the detection optical path to direct emission energy from the sample plate to a detector. In a number of implementations, the detector is positioned in the detection optical path and is capable of detecting emission energy from the sample plate. In various implementations, the emission energy is fluorescent emission and the fluorescent emission is directed to the detector from the multifunction mirror. In some implementations, the system further includes an emission filter slide including at least one emission filter. According to certain implementations, the emission filter slide is positioned in the detection optical path between the multifunction mirror and the detector. In accordance with a number of implementations, the emission filter slide includes four emission filters, wherein each emission filter filters a different wavelength. In various implementations, the system further includes an emission filter motor for moving the emission filter slide.

In certain implementations, the set of excitation optics includes an excitation filter and two lenses. In some implementations, the system further includes a movable lid that is positioned to move around the optical assembly and wherein the movable lid includes a heated lid configured to mate with the sample plate. In some implementations, the thermal assembly includes a thermal block that includes the sample plate. According to a number of implementations, a liquid composition occurs within the thermal block and external to the sample plate.

In certain implementations, the system further includes: (a) two excitation source assemblies positioned in the excitation optical path, wherein an excitation source assembly includes individual light emitting diodes (LEDs) corresponding to individual wells on the sample plate; (b) a multifunction mirror positioned in the excitation optical path to direct excitation energy from individual LEDs to the corresponding individual wells of the sample plate and wherein the multifunction mirror is further positioned in the detection optical path to direct fluorescence emission from the sample plate to a detector; and (c) an emission filter slide positioned in the detection optical path between the multifunction mirror and the detector, wherein the emission filter slide includes at least one emission filter. In accordance with a number of implementations, the excitation optical path comprises two excitation source assemblies and two sets of excitation optics. In some of these implementations, each set of excitation optics comprises an excitation filter and two lenses.

In some implementations, each excitation source assembly includes an LED backplate to which an LED array including the LEDs is mounted, a lenslet array including individual lenslets corresponding to individual LEDs in the LED array, wherein the lenslet array is positioned to transmit the excitation energy from the LEDs on the LED array to the multifunction mirror and an excitation source cooling portal positioned to cool the LED backplate. In some implementations, the emission filter slide includes four emission filters, each emission filter filtering a different wavelength. In accordance with various implementations, the system further comprising an emission filter motor for moving the emission filter slide. According to a number of implementations, the system further includes at least one detection lens assembly positioned between the emission filter slide and the detector. In some implementations, the system further includes a movable lid that is positioned to move around the optical assembly and wherein the movable lid includes a heated lid configured to mate with the sample plate.

In certain implementations, the thermal assembly includes a thermal block comprising the sample plate. In some implementations, a liquid composition occurs within the thermal block and external to the sample plate.

In another aspect, a system comprises an optical assembly in a fixed position relative to a thermal assembly configured to hold a sample plate, wherein the system comprises a movable lid that moves around the optical assembly, and wherein the movable lid comprises a heated lid configured mate with the sample plate. In some instances, the optical assembly comprises at least one excitation optical path and at least on detection optical path, wherein the excitation optical path and the detection optical path are in the same plane.

In some instances, the optical assembly comprises a multifunction mirror that directs excitation energy to the sample plate from the at least one excitation optical path and that directs emission energy from the sample plate to the detection optical path. The optical assembly can comprise at least one excitation source, wherein the excitation source comprises one LED corresponding to each well on the sample plate. In some instances, the optical assembly comprises a detector capable of detecting fluorescent emission from the sample plate.

In some instances, the thermal assembly comprises a closed liquid reservoir and a stirrer in thermal contact with a heater. In some instances, the sample plate comprises 48 wells.

In some instances, the movable lid is a hinged lid. The movable lid can further comprise an optical component, for example, a Fresnel lens. In some instances, the movable lid further comprises a spring-like or flexible component configured to improve the thermal contact of the heated lid to the sample plate.

In yet another aspect, a system comprises an optical assembly configured to excite a biological assay and to detect emission from the biological assay, wherein the optical assembly comprises at least one excitation optical path and at least on detection optical path, wherein the excitation optical path and the detection optical path are in the same plane. In some instances, the optical assembly comprises at least one excitation source, wherein the excitation source comprises one LED corresponding to each well on the sample plate. In some instances, the optical assembly comprises a detector capable of detecting fluorescent emission from the sample plate.

In some instances, the optical assembly comprises a multifunction mirror that directs excitation energy to the sample plate from the at least one excitation optical path and that directs emission energy from the sample plate to the detection optical path.

The system can further comprise a thermal assembly configured to thermally cycle the biological assay. In some instances, the thermal assembly comprises a closed liquid reservoir and a stirrer in thermal contact with a heater.

For purposes of summarizing the disclosure, certain aspects, advantages and novel features of the inventions have been described herein. It is to be understood that not necessarily all such advantages may be achieved in accordance with any particular embodiment of the invention. Thus, the invention may be embodied or carried out in a manner that achieves or optimizes one advantage or group of advantages as taught herein without necessarily achieving other advantages as may be taught or suggested herein.

BRIEF DESCRIPTION OF THE DRAWINGS

Many features of the invention are set forth with particularity in the appended claims. A better understanding of the features and advantages of the invention will be obtained by reference to the following detailed description that sets forth illustrative embodiments, in which many principles of the invention are utilized, and the accompanying drawings of which:

DETAILED DESCRIPTION

Figure 1:
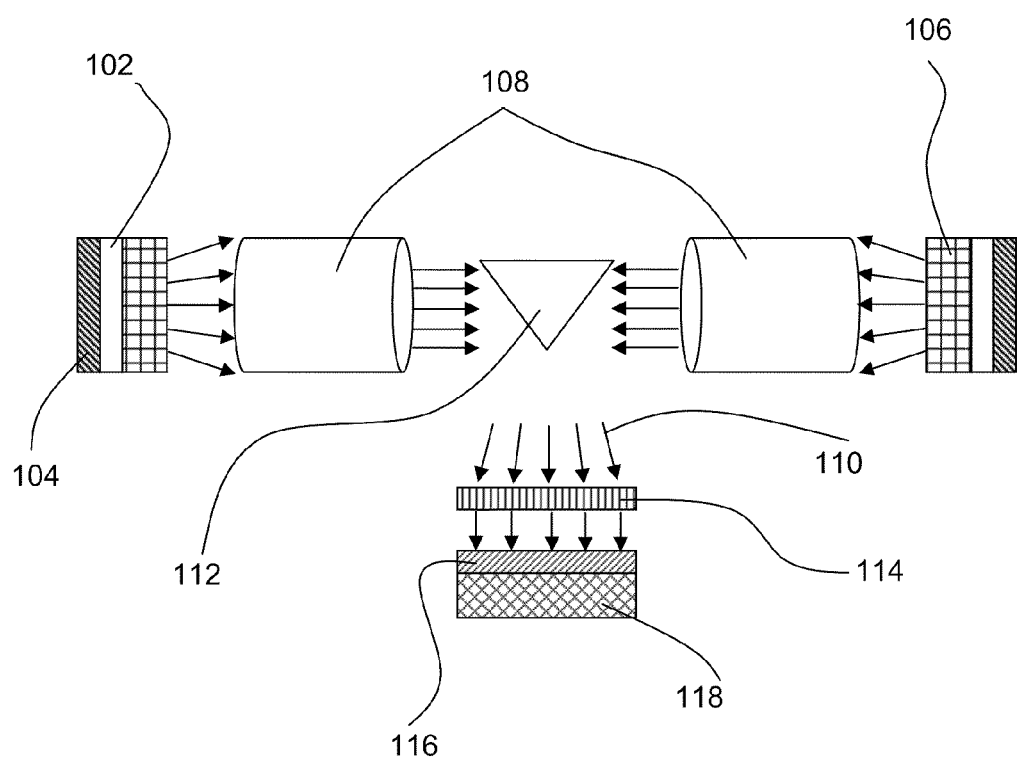
FIG. 1 illustrates an exemplary excitation optical path of the optical system as described herein.

Described herein are a devices, methods, and systems for measuring multiple chemical reactions in multiwell plates. An optical assembly of systems herein can comprise multiple light sources, such as light emitting diodes (LEDs). In the optical assembly, each light source, for example an LED, corresponds to a sample vessel on the multiwell plate.

Example embodiments of the invention described herein utilize particular arrangements of optical elements such as lenses, filters, and reflectors. There are many other optical arrangements which can be implemented in order to carry out or construct aspects of the disclosure that would be understood by one of ordinary skill in the art for directing the light beams to the corresponding sample vessels and for directing light from the sample vessels to a detector.

Where the optical system has an excitation source array, a detector, and the appropriate filters, lenses, and reflectors, the system can be used as a fluorometer. A fluorometer provides excitation light to a sample and detects the light emitted from fluorescent entities within the sample.

Also disclosed herein are systems for the controlled heating of samples such as biological samples for thermal cycling reactions. The devices herein can offer improved temperature uniformity and distribution to current technology in the art. Temperature uniformity can be highly desirable in PCR reactions, for example, where a plurality of samples in a plurality of reaction containers are advantageously cooled or heated simultaneously.

In addition to heating of PCR samples, the devices and methods herein can be used widely in the field of biotechnology and chemistry. Examples include but are not limited to incubations of enzymatic reactions such as restriction enzymes, biochemical assays and polymerase reactions; cell culturing and transformation; melting of nucleic acids; hybridization; and any treatment requiring precise temperature control. Based on the present disclosure, one of ordinary skill in the art can readily adapt the disclosed technology to various analyses of biological/chemical samples which require accurate temperature control.

In some instances, a system as described herein can further comprise an optical assembly having a light source and an optical detector, wherein the optical assembly is positioned such that light from the light source is directed into the sample holder, and light from the sample holder is detected by the detector. The detector of the optical assembly can comprise a PIN photodiode, a CCD imager, a CMOS imager, a line scanner, a photodiode, a phototransistor, a photomultiplier or an avalanche photodiode. The excitation source can comprises one or more LEDs, laser diodes, vertical cavity surface emitting lasers (VCSELs), vertical external cavity surface emitting lasers (VECSELs), or diode pumped solid state (DPSS) lasers. In some embodiments, the optical elements can be arrays of light emitting diodes (LEDs). LEDs have advantages as light sources for the optical systems provided herein in that they are small, relatively inexpensive, generate relatively low heat, and can provide light in the spectral ranges required for measuring samples, for example by fluorescence.

An optical detector as described herein can comprise a plurality of optical detectors, wherein at least one optical detector corresponds to a sample well in a sample microplate.

An apparatus herein can also further comprise a control assembly which controls the apparatus, the light source, and the detector. In some instances, the control assembly comprises a programmable computer programmed to automatically process samples, run multiple temperature cycles, obtain measurements, digitize measurements into data and convert data into charts or graphs.

FIG. 1 illustrates an example excitation optical path of the optical system as described herein. As shown in FIG. 1, the excitation path can comprise two LED arrays 102 mounted on a backplate 104. As described herein, the LED array assembly can be cooled by cooling the backplate 104 on which the LED arrays 102 are mounted. In an embodiment, the LED arrays 102 emit the same color or wavelength of excitation energy. In another embodiment, the LED array 102 emits a different color or wavelength of excitation energy, for example, one array emits blue excitation energy and the other array emits green excitation energy. The excitation energy from the LED array 102 travels through a lens array 106. In an embodiment, the lens array 106 is a lenslet array, comprising a lenslet corresponding to each LED in the LED array 102, for example, 48 lenslets for 48 LEDs. After travelling through the lens array, the excitation optical path travels through excitation optics 108 which can include without limitation filters, lens, or fiber optics. The excitation energy 110 is directed by the multifunction mirror 112 towards the thermal block. As demonstrated in FIG. 1, the multifunction mirror 112 can have at least two faces in the excitation path, each face corresponding to an LED array. A Fresnel lens 114 or other optical device can be mounted above or coupled to a heated lid cover 116 for the sample plate 118. In an embodiment, the Fresnel lens 114 and the heated lid are incorporated into a hinged lid that moves over and around a stationary optical assembly. The excitation energy 110 is directed into the sample plate 118 which is mounted into a thermal block as shown in FIG. 1. In an embodiment, the optical assembly comprises two fixed LED systems and four emission filters to support standard dyes, including without limitation SYBR Green I, FAM, HEX, ROX, and Cy5.

Figure 2:
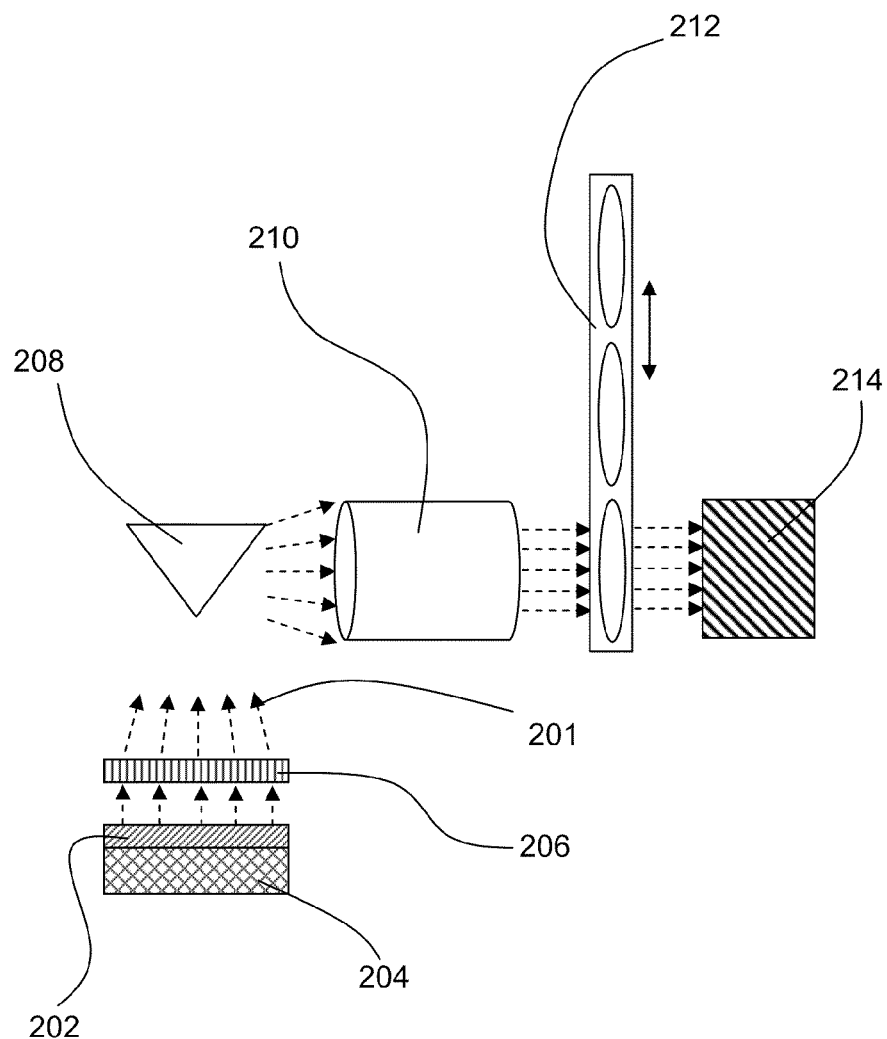
FIG. 2 illustrates an exemplary embodiment of the detection optical path of the optical system as described herein.

FIG. 2 illustrates an example embodiment of the detection optical path of the optical system as described herein. As demonstrated by FIG. 2, emission energy 201 is emitted from the sample in the sample wells of the sample plate 204, for example, by fluorescence. The emission energy 201 travels back through the heated lid cover 202 of the sample plate 204, through the Fresnel lens 206 and to the multifunction mirror 208. In an embodiment as demonstrated herein, the multifunction mirror 208 is the same multifunction mirror 112 as demonstrated in FIG. 1, wherein the multifunction mirror is a three-sided mirror to allow both the excitation optical path and detection optical path to be in the same plane in the optical assembly. In another embodiment, the multifunction mirror 208 is a different mirror than that in the excitation optical path. As demonstrated in FIG. 2, the detection optical path travels through the detecting optics 210 which can include without limitation lenses, fiber optics, and optical filters. The optical path can then optionally travel through an optical filter. In the example of FIG. 2, the optical detection filter 212 is a single longitudinal device with multiple filters that can be moved in the path to filter different wavelengths of energy. For example, depending on the wavelength of the detection dye used in the sample plate, the optical detection filter 212 can be changed to filter out any excess noise not in the color range of the dye. The detection optical path ends at the detector 214, where the emission energy from the sample plate can be detected to complete an assay with the system as described herein. The detector 214 is positioned in the detection optical path and is capable of detecting emission energy from the sample plate. In some instances, the emission energy is fluorescent emission and the fluorescent emission is directed to the detector from the multifunction mirror 208.

Figure 3:
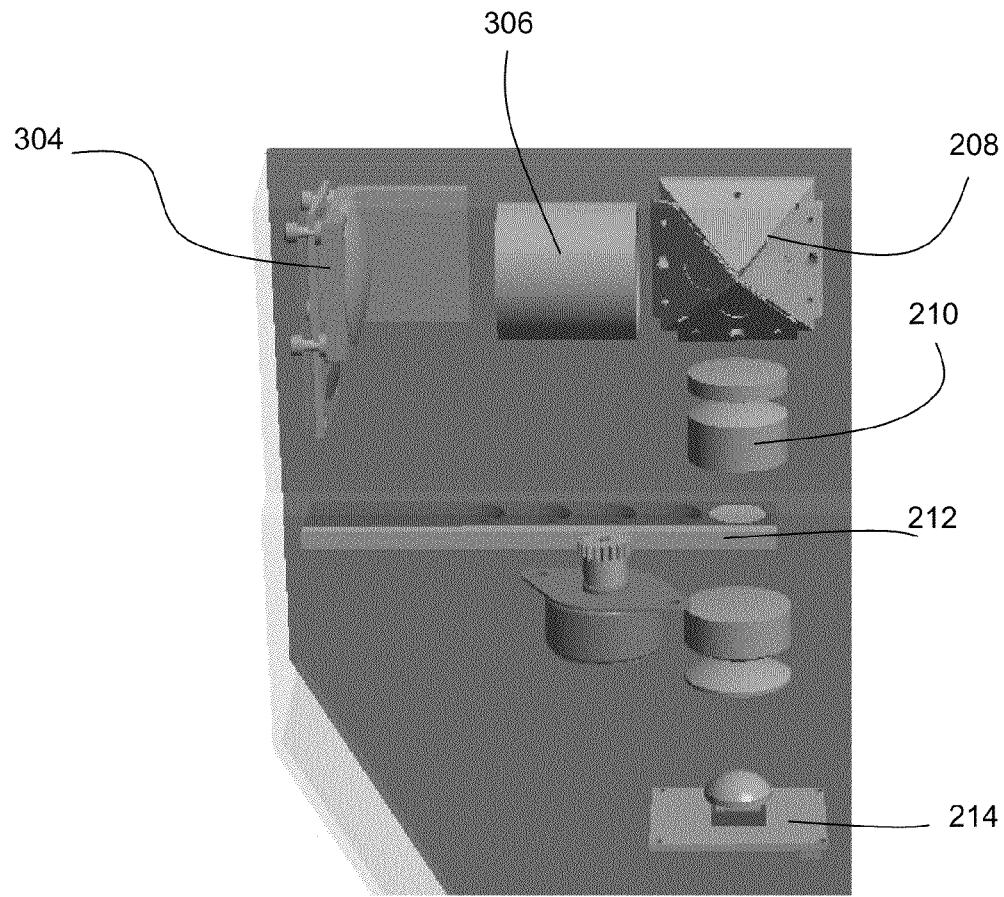
FIG. 3 shows another view of the detection optical path from the plane of the multifunction mirror.

FIG. 3 demonstrates another view of the detection optical path from the plane of the multifunction mirror 208. The excitation assembly, including an excitation source assembly 304 and excitation optics 306, is in the same plane as the detection optics 210 in FIG. 3. As illustrated, the excitation assembly is positioned in the excitation optical path. The excitation assembly provides excitation energy through the excitation optics 306 to the multifunction mirror 208 which directs the energy to the sample plate. In some implementations, the components of the excitation assembly are substantially similar to their corresponding components described above with reference to FIG. 1. Emission energy returns from the samples in the sample plate through the multifunction mirror 208, which then sends the emission energy through a series of detection optics 210 in the detection optical path including a detection filter of the detection filters 212, as described above, to the detector 214. Thus, the multifunction mirror directs excitation energy to the sample plate from the excitation optical path and directs emission energy from the sample plate to the detection optical path. In addition, as illustrated, the multifunction mirror is positioned in the excitation optical path to direct excitation energy from each LED to the corresponding well of the sample plate and is further positioned in the detection optical path to direct emission energy from the sample plate to the detector.

Figure 4:
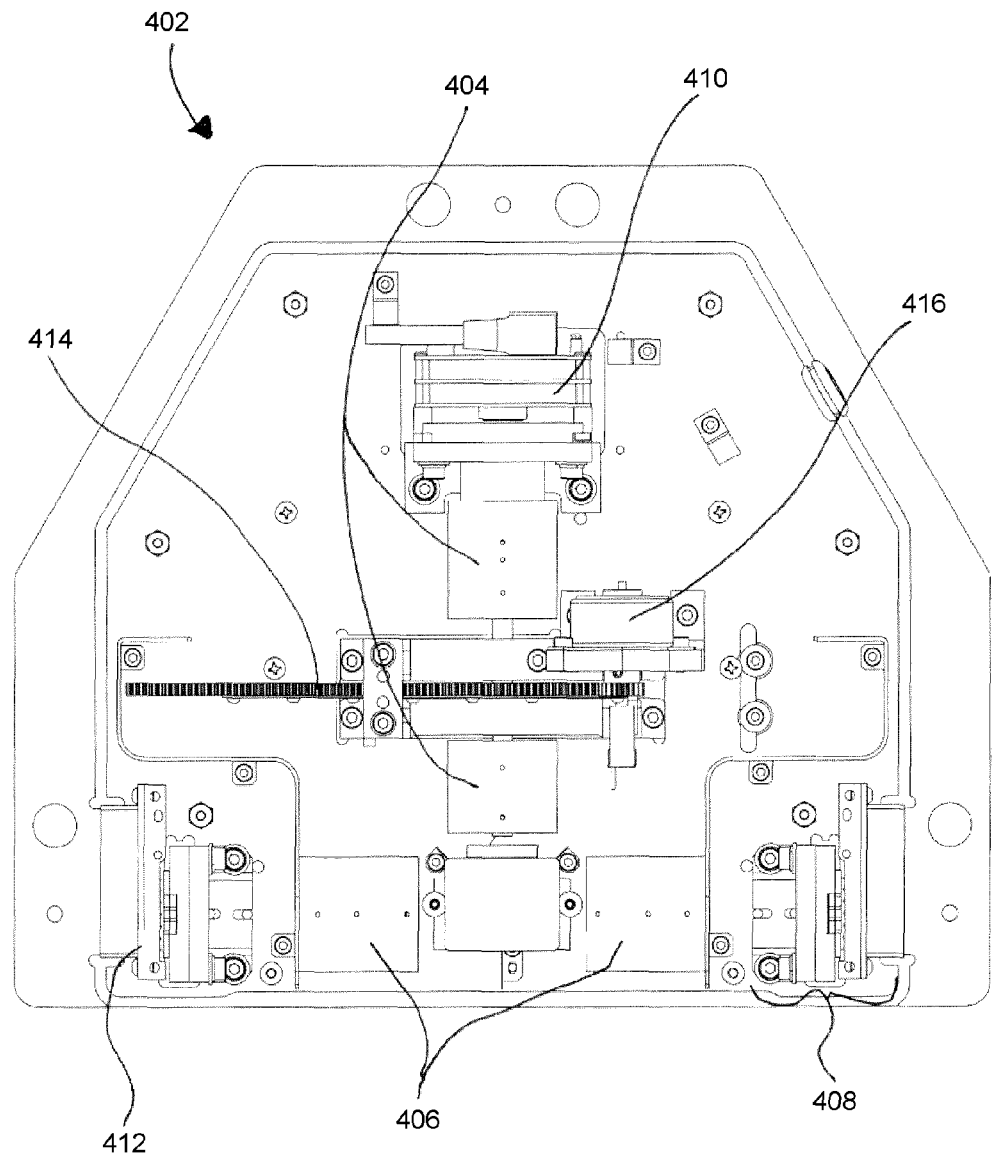
FIG. 4 displays an exemplary optical assembly as described herein comprising both detection optics and excitation optics in the same plane.

FIG. 4 displays an example optical assembly 402 as described herein comprising both detection optics 404 and excitation optics 406 in the same plane. In particular, a fixed excitation source assembly 408 directs light through the excitation optics 406 in the same plane as light is received by the fixed detection optics 404. As illustrated in FIG. 4, two sets of excitation source assemblies 408 can generate optical signals in the same plane as one or more optical signals received by the detector 410. Moreover, the source assemblies 408 and the detection optics 404 and/or the detector 410 are also in the same plane in the illustrated embodiment. As displayed, the excitation source assembly 408 comprises an LED array. The LED array is mounted on an LED backplate 412. In some instances the LED backplate 412 comprises aluminum. In some instances, the LED backplate 412 is heat conductive and transfer heat away from the LED array. Also demonstrated in FIG. 4 are excitation optics 406, detection optics 404 including emission filters, and a detector 410. In some instances, the emission filters are mounted on an emission filter slide 414. As illustrated, the emission filter slide 414 is positioned in the detection optical path between the multifunction mirror and the detector 410. The emission filter slide 414 can be moved by an emission filter motor 416, for example as shown in FIG. 4. In some instances, the emission filter slide 414 comprises 5 emission filters for filtering 5 different wavelengths. In some instances, the emission filter slide 414 comprises 1, 2, 3, or 4 emission filters. In some instances, the emission filter slide 414 comprises 6 or more emission filters. In some instances, the emission filter slide 414 comprises emission filters, wherein each emission filter filters a different wavelength. In some instances, the emission filter slide 414 comprises at least 2 emission filters that filter the same wavelength. As shown in FIG. 4, the detector 410 is mounted after the detection optics 404.

Figure 5:
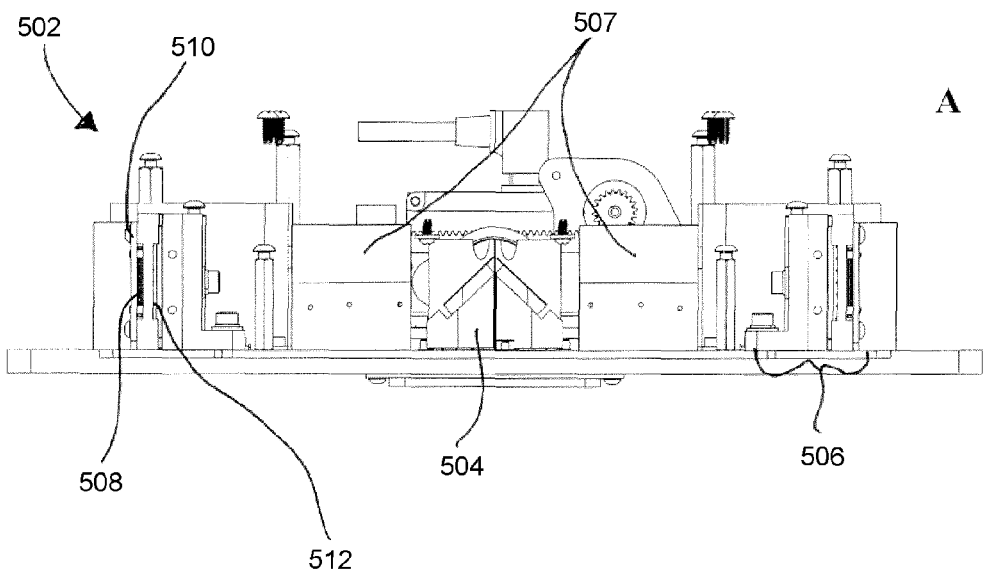
FIGS. 5A-B are side views of an exemplary optical assembly as described herein.
Figure 5:
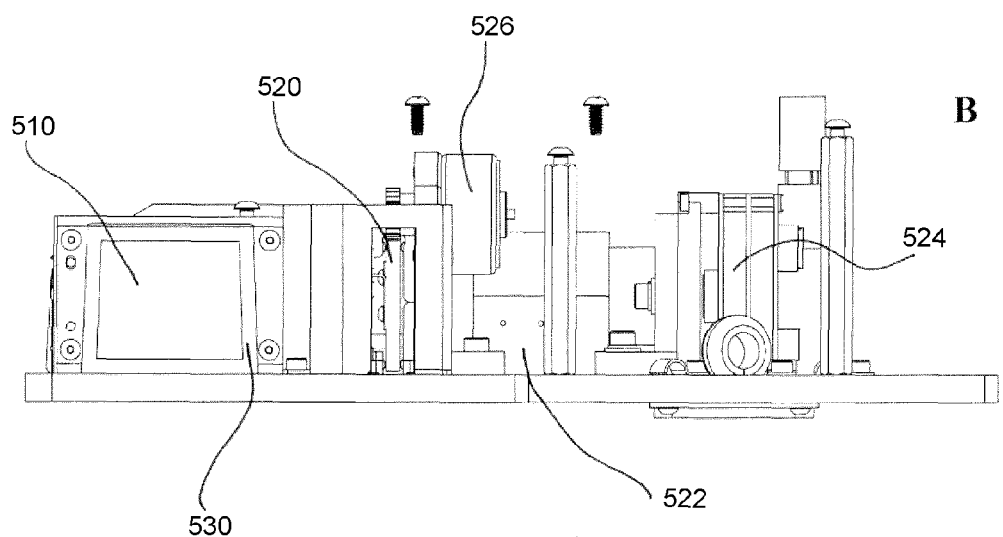

FIGS. 5A-B illustrate a side view of an example optical assembly 502 as described herein. FIG. 5A displays an optical assembly comprising a multifunction mirror 504 in the excitation optical path. The multifunction mirror 504 directs light from the excitation source (for example, LED array) in an excitation source assembly 506 to a sample holder and also direct light from the sample holder to the detector. The excitation optical path from the excitation source to the multifunction mirror 504 comprises excitation optics 507 that are capable of directing the light, filtering the light, or shaping the light. In some instances such as in FIG. 5A, the excitation source assembly 506 comprises an LED array 508 mounted on an LED backplate 510 and a lenslet array 512 for directing the energy from the LED array 508 to the excitation optics 507 in the optical path. FIG. 5B illustrates another example side view of an optical assembly herein, displaying the detection optical path. The detection optical path comprises an emission filter slide 520 comprising emission filters for different detection wavelengths and detection optics 522 that are capable of directing the light, filtering the light, or shaping the light to the detector 524. The emission filter slide 520 can be moved by an emission filter motor as demonstrated in FIG. 5B. FIG. 5B also displays a back view of the excitation source assembly. In some instances, the excitation source assembly comprises an LED array mounted on an LED baseplate 528. The excitation source assembly can comprise an excitation cooling portal 530, which allows for cooling of the excitation source. When the excitation is an LED array mounted on a baseplate 528, the LED array can be actively cooled through the excitation cooling portal 530.

Figure 6:
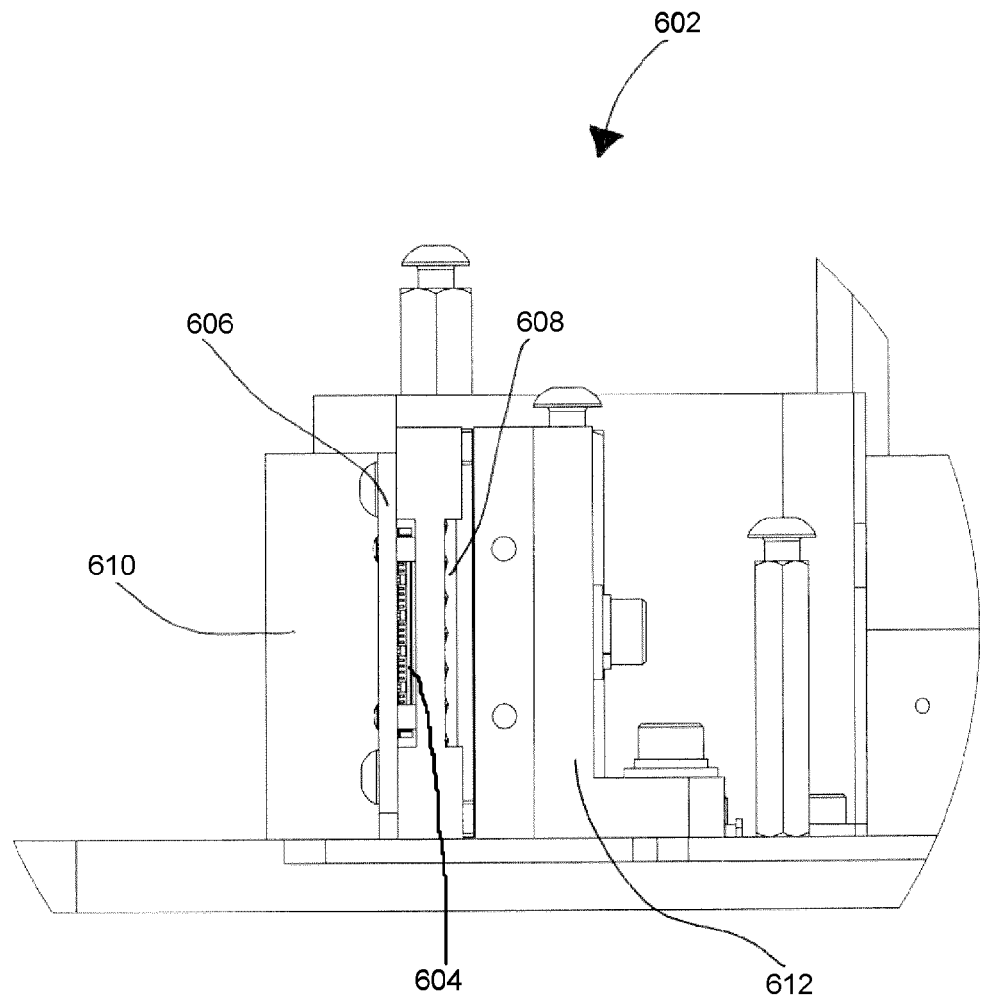
FIGS. 6 and 7 display a view of an exemplary excitation source assembly herein.
Figure 7:
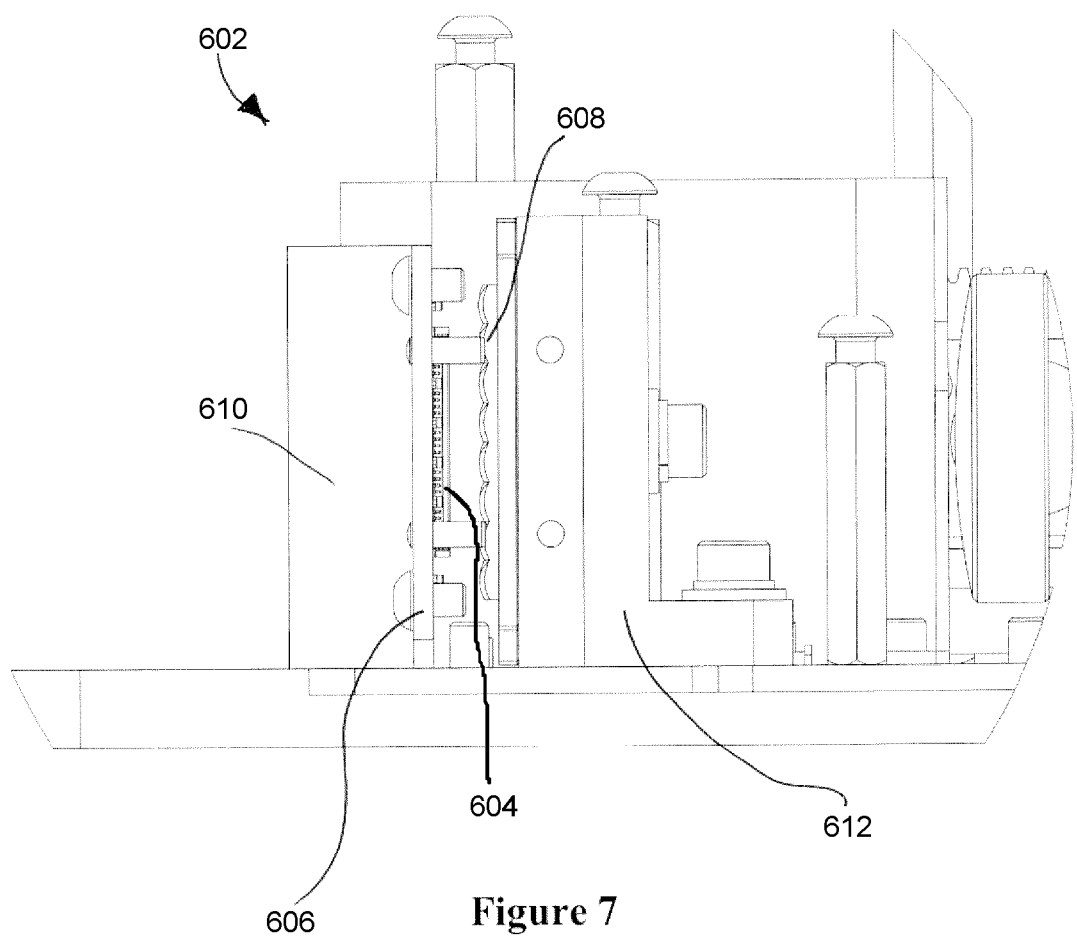

FIGS. 6 and 7 display a view of an example excitation source assembly herein. The excitation source assembly 602 comprises an LED array 604, an LED baseplate 606, a lenslet array 608, and an excitation source cooling portal 610. In some instances, the excitation source assembly 602 also comprises an adjustment assembly 612 that permits moving the assembly in three dimensions in order to position the excitation source assembly 602. The adjustment assembly 612 can be moved to align the excitation optical path with the excitation optics of the optical assembly 602.

Figure 8:
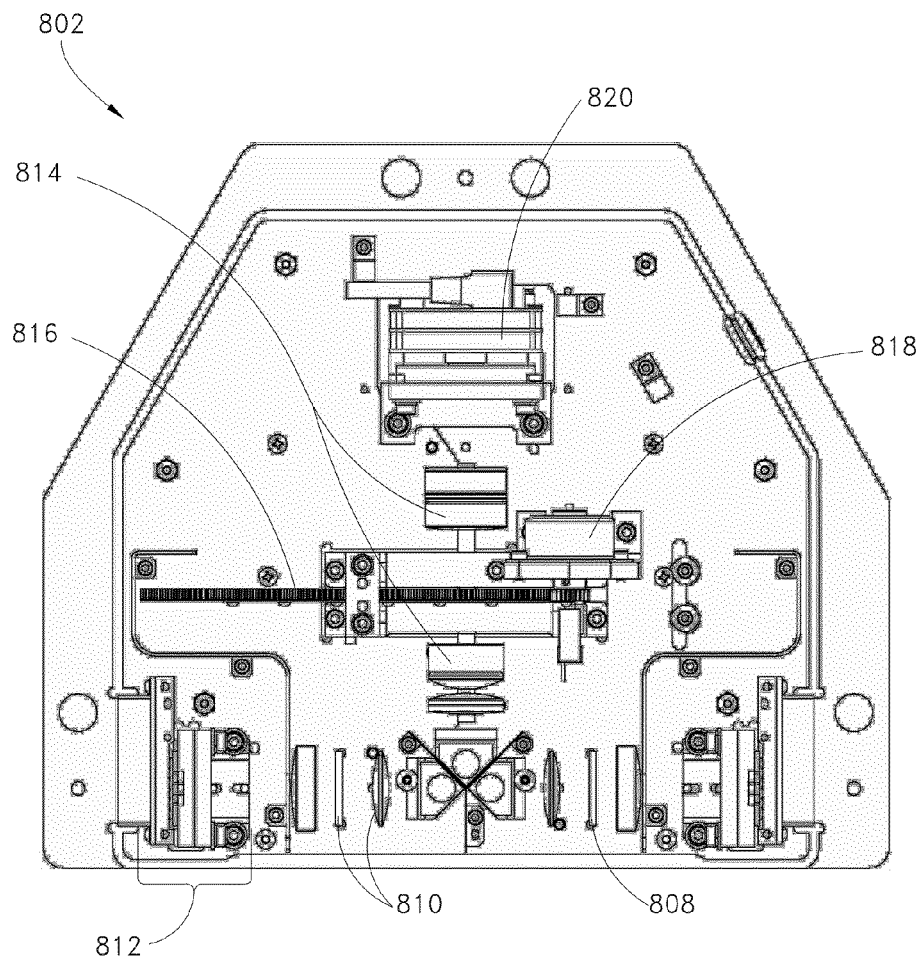
FIGS. 8 and 9 display another exemplary optical assembly as described herein comprising both detection optics and excitation optics in the same plane.
Figure 9:
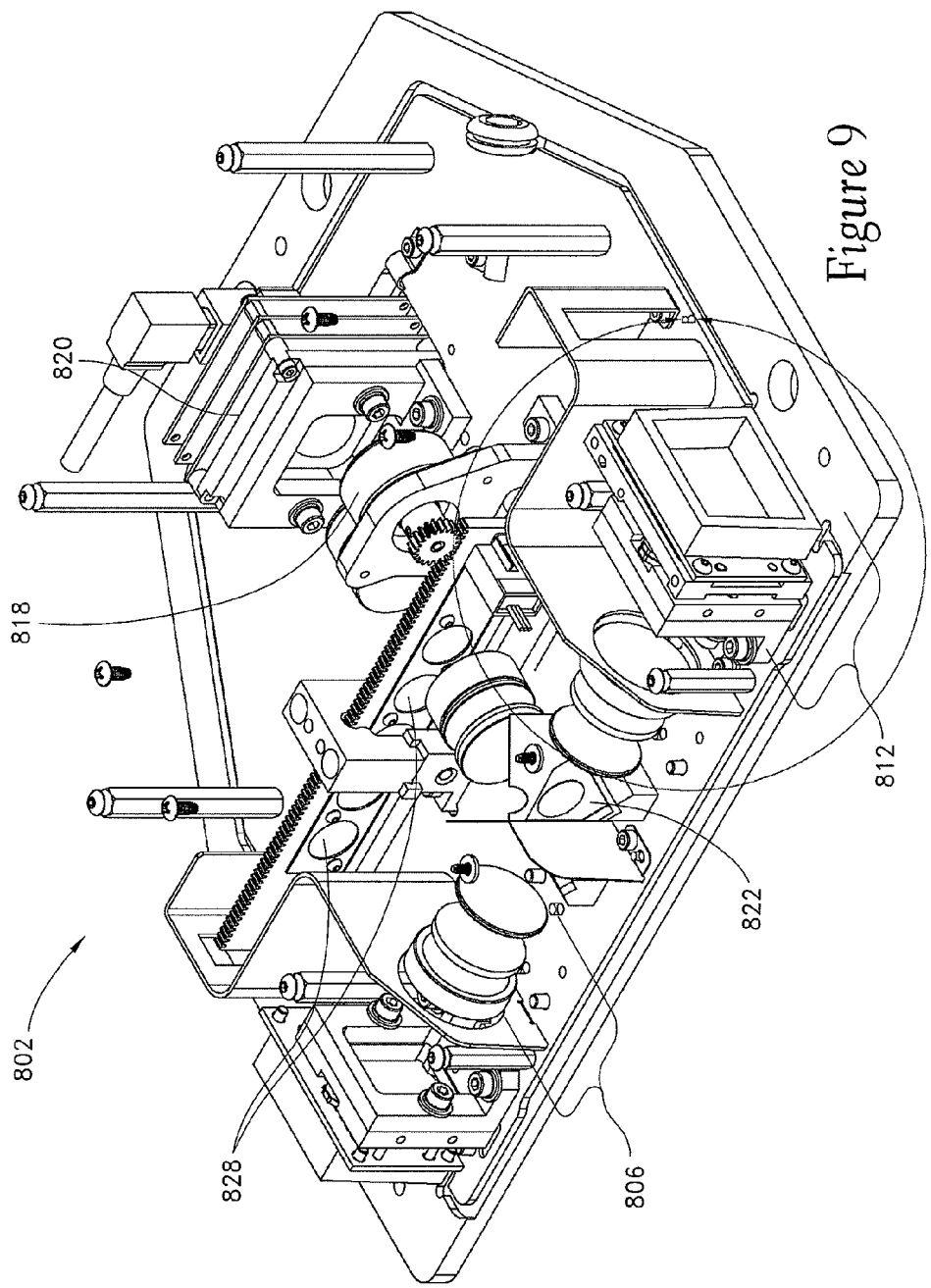

FIGS. 8 and 9 display another example optical assembly 802 as described herein comprising both detection optics 804 and excitation optics 806 in the same plane. In some instances, the excitation optics 804 comprise an excitation filter 808 and two lenses 810. In certain instances, the excitation filter 808 is positioned between the two lenses 810. The excitation filter 808 is chosen based on the wavelength of the excitation light source and the assay to be run in the sample holder. In the examples of FIGS. 8 and 9, the optical assembly 802 comprises two excitation source assemblies 812 and two sets of excitation optics 806. In some instances, the excitation source assemblies 812 provide two different wavelengths of excitation light and the excitation optics 806 can correspond to the different wavelengths. In some instances, the excitation source assemblies 812 provide the same wavelengths of excitation light. Also demonstrated in FIG. 9 are detection optics 804 comprising two detection lens assemblies 814 and an emission filter slide 816 comprising emission filters 828. The emission filter slide 816 can be moved by an emission filter motor 818. This can change which emission filter 828 is in the detection path. A detector 820 and a multifunction mirror 822 are also illustrated in FIGS. 8 and 9.

Figure 10:
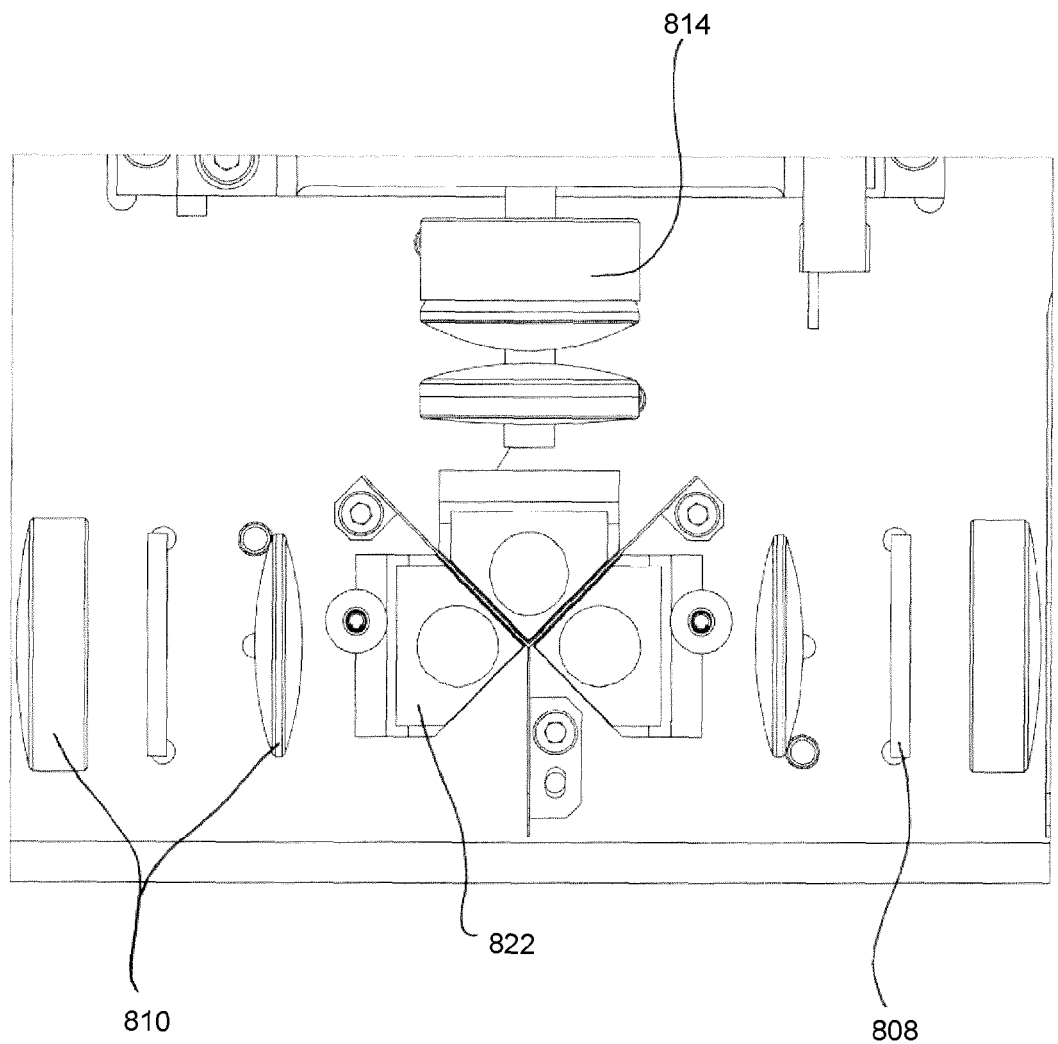
FIG. 10 provides a zoomed view of the multifunction mirror and the excitation and detection optics.

FIG. 10 provides a magnified view of the multifunction mirror 822 and the excitation and detection optics 806, 804, respectively, illustrated in FIGS. 8 and 9. The multifunction mirror 822 allows for the detection and excitation optics 806, 804, respectively, to be in the same plane as the excitation source assembly 812 and/or the detector 820 of the optical assembly 802. The excitation optics 806 comprise an excitation filter 808 and two lenses 810. The detection optics in FIG. 10 comprise a lens assembly 814. As illustrated, the system includes the multifunction mirror 822, the two excitation source assemblies 812, and the two sets of excitation optics 806; in the excitation optical path, one excitation source assembly and one set of excitation optics is positioned on one side of the multifunction mirror 822 and another excitation source assembly and another set of excitation optics is positioned on another side of the multifunction mirror 822.

In real-time PCR, fluorescence measurements of a sample mix are made after the PCR amplification step (or sometimes more often) in order to track the amount of PCR product generated. Details vary according to the PCR chemistry being used, but typically a baseline fluorescence level increases to a final fluorescence level which is several orders of magnitude more intense at the end of the run, the increase being exponential in the interesting portion of the run. Quantitation typically consists of determining the fractional cycle number at which the fluorescence of the reporter dye increases by a predetermined small fraction of the baseline level; this requirement puts a premium on the stability of the fluorescence signal over many cycles, as well as requiring sufficiently low random noise. Noise sources intrinsic to the PCR process, such as starting copy number statistics and amplification noise, place a lower limit on the degree to which improved radiometric and other detection system noise can improve overall quantitative precision.

In the real-time PCR systems described herein, many (for example, 48) PCR samples are amplified simultaneously in a 2-D plate format, and the detection system accommodates this parallelism. In some embodiments, ease of alignment and calibration, measurement speed, robustness and reliability are important drivers in addition to adequate quantitative performance. In many cases, multiple dyes (for example, up to about 4) are measured in each sample, either to track multiple reactions within each well (multiplexing) or to accommodate various multi-dye chemistries. This requirement significantly complicates the optomechanical design. A number of commercial real-time PCR instruments have been marketed for many years, using a variety of detection schemes.

In some instances, a system herein has minimal moving parts and the optical system is fixed relative to the thermal block. In addition, a device, as demonstrated herein can be configured to be robust in regards to shock and vibration during shipment or in operation. In some instances, a system herein for real-time PCR can operate at a quick speed, and have very good reproducibility and stability. In some embodiments, switching from dye channel to dye channel can be done instantaneously, allowing measurements of different dyes to be interleaved when simultaneity is important.

Excitation and emission beams at the sample in fluorescence detection systems can overlap using beam splitters. These beam splitters may be either dichroic (spectrally selective) or neutral. Beam splitters offer the advantage of maximizing the excitation and emission etendues where etendues are limited by the well geometry rather than source or detector factors. Also, dichroic splitters allow nearly full transmission for both excitation and emission beams when designed for a wavelength transition between the dye excitation and emission bands, and can therefore be radiometrically efficient. However, dichroic beamsplitters have a couple of problems, such as: (a) typically operating at 45 degrees, they exhibit very high angular sensitivity of the transition wavelength, making them hard to design for a large field (many well) system, and (b) usually only a single excitation wavelength can be accommodated with a given dichroic. The latter restriction means that for a multiple dye system, the excitation should be at a single wavelength, to the blue of the shortest wavelength dye, or else the beamsplitter should be changed (via mechanical motion) for each dye measurement, or finally a complex set of sequential dichroic beamsplitters should be engineered. Using a single excitation wavelength means that some of the dyes are very inefficiently excited, and that an unfavorable ratio of emission intensities is likely—making dye-dye crosstalk effects more difficult to untangle. Neutral beamsplitters (such as 50%/50%) do not suffer these disadvantages, but do result in at least 4× smaller signal levels. All beamsplitter designs also place an additional optical component, generally with two surfaces, in the common beam paths. This component is a potential source of parasitic fluorescence and of direct scattering from the excitation source into the detection channel.

An alternative approach which avoids most of these problems is to separate the excitation and emission beams geometrically, and perhaps also the excitation and/or emission beams corresponding to different dye channels. Since the beams should overlap at the sample, the separation is normally done at the complementary stop, also referred to as the multifunction mirror herein. In other words, the solid angle space as seen from the sample volume is divided up geometrically among n=2 or more beams. This results in a signal reduction of ~n—assuming that the source and detection optics, including any filters, had sufficient etendue to match the full etendue of the sample well in the first place. If not, the signal reduction factor is lower than n. This radiometric hit is similar to that using neutral beamsplitters, but with the very large advantage that the etendue requirements for the source and detection optics (including their lenses and filters) are much smaller. This means cheaper, smaller optics, and often less difficulty with aberration control. The beamsplitters themselves are also eliminated, of course, although generally some pupil division optic (mirror or prism) would still be implemented.

In many cases, plate readers employing simultaneous imaging of the full plate use a single relatively powerful source to illuminate all wells. This can be a laser, filtered arc or tungsten lamp, or a high power LED, among other possibilities. From the standpoints of cost, longevity, heat and power consumption, stability, and timing control; LED sources are highly desirable. While it is possible to employ multi-die high powered LED sources capable of illuminating a full well plate with somewhat adequate irradiance, an attractive and obvious alternative is to use an array of low cost, low power LEDs whose dies can be imaged directly into the sample wells.

In some instances, by exercising independent control of multiple excitation sources, large system advantages can be obtained, as described below. The basic advantages of array illumination are that low cost devices, potentially available in a wider variety of wavelengths to match the excitation spectra of more dyes, can be used, and that by confining illumination to the active regions of the individual wells, one can avoid many problems of well-well overlap and crosstalk, including effects of parasitic fluorescence in construction materials.

The overall power efficiency can also be improved; less total input power per unit of useful illumination.

Issues with multiwell real-time PCR include a limited dynamic range. Different wells may have fluorescent emission fluxes which differ by up to 2 to 3 orders of magnitude, and similar ratios may apply between individual dyes in the same well. This means that stray light from well A to well B should either be very tightly controlled or somehow compensated for in data analysis, lest large error appear in PCR results. Only a small amount of crosstalk, can have very serious effects on baseline wells in comparison to typical radiometric noise levels which otherwise determine quantitative precision. Stray light can be due to scattering within the well plate plastic itself, or from optical elements in the light path above the well plate. Multiple specular reflections from optical surfaces can also produce significant crosstalk, often between highly-separated wells.

A second effect of the dynamic range encountered across a plate is that in order to achieve adequate signal to noise ratios at the various fluorescence intensities, CCD or CMOS array detectors are generally operated at several integration times, a relatively long one for weaker wells, together with at least 1 or 2 shorter exposures to accommodate intense wells without detector pixel saturation. This results in additional data transfers and additional measurement time. More significantly, the intense wells will strongly saturate the detector during the longest exposure times, meaning that array detectors having extremely efficient anti-blooming performance may be chosen. Also, of course, the purely optical part of the cross-talk cannot be eliminated in this way in any case. It is possible (and may be necessary in some instances) to provide software compensation for crosstalk, based on measured system crosstalk data.

Independent time gating of excitation LEDs allows a single array detector integration time can be used, with the temporal duty factor of the LEDs adjusted per-well to achieve nominally similar exposures for each well (say 50-75% of full well for pixels in the middle of each well image). Thus, wells emitting only baseline fluorescence levels can have their LEDs turned on 100% of the time (one die at a time), whereas very intense wells may have their LEDs on during only 1% or less of the integration time. On a time averaged basis, crosstalk between wells becomes negligible, and what little there is becomes highly consistent over time. Array pixels rarely become saturated. Since detection is always at a large fraction of well capacity, array read noise becomes relatively unimportant, and the system should become shot noise limited for all wells. Moreover, the resulting noise level will be the same as what would otherwise have been obtained for the baseline wells, and it is the noise at or near baseline which determines PCR quantitative performance. Some measurement time is saved by eliminating the multiple exposures, allowing either the PCR cycles to be speeded up or allowing for more array reads to be summed for improved signal-to-noise ratios.

One enabler of this LED gating approach is that the PCR emission signal is inherently smooth as a function of cycle number. Thus, the change in signal from cycle to cycle is relatively small, except in the strongly exponential phase. However, even in this phase the signal at the next cycle can still be well predicted from the previous cycles. Thus a prediction algorithm can be used to decide what LED duty factor to employ for each new measurement, to within say ±30%, with little or no risk of overexposure. Alternatively or additionally, a very short pre-exposure could be used to determine the LED duty factor. Using this scheme, the fluorescence signal used for PCR quantitation is composed of two multiplicative factors: the LED duty factor that was employed is the main component, with the array detector signal summed over the pixels making up the region of interest (ROI) for a well acting as a vernier adjustment factor. The detector signal contributes almost all the noise since LED timing can be highly accurate and reproducible.

Many detectors, as described herein capable of on-chip electronic shuttering, make use of microlenses to increase effective quantum efficiency. An important side effect of the use of microlenses is to reduce the effective angular acceptance range of each pixel of the array. In many examples, the microlenses are situated such that the peak signal is obtained at normal incidence, and beyond a certain off-axis angle, symmetrically disposed about the normal, response falls off rapidly. Usually the angular width is different along the two orthogonal axes of the sensor.

The effect of this microlensing shading is to place a fairly severe limit on the practical numerical aperture (NA) of the camera optics, and to require that for best results the lens be telecentric at the sensor. For a given sensor area (driven by economics), the area combined with the limiting NA defines a practical maximum system etendue. Because of this, the multifunction mirror can be implemented in a system herein with minimal penalty.

That is, the etendue allowed by sensor microlensing is readily accommodated in a pupil shared system with up to at least 3 separate excitation beams, without any compromise. Under these circumstances, use of dichroic beamsplitters (which incur numerous disadvantages) would not result in any signal increase as compared to a multifunction mirror.

The excitation power which can be delivered to a well using the one-LED-per well as described herein is effectively the radiance of an LED die (limited by available LED technology at required wavelengths, more or less independent of die size), multiplied by the excitation optics per-well etendue. This per-well etendue depends on the image size of the LED die in the well, as well as the pupil area. The actual size of the source LED die may not matter, although there are practical optically determined limits on how small the dies can be while maximizing the image size at each well.

When LEDs are widely spaced in the source array, using available discrete surface mount packages, the fractional area of the source array actually filled by the emitting dies is small. Using a simple objective, imaging the full LED array 1:1 onto the well plate, the die image sizes are quite small, a small fraction of the well diameter, and hence the excitation power is less than it could be.

In some instances, the optics of the excitation optical path comprise composite optics, in which a simple objective images the full array, while a lenslet associated with each LED permits local magnification of the LED image so that a normally die size (typically 300 um square) can essentially fill the active portion of a microwell (~2 mm diameter). With this solution, the NA at each source LED is relatively high, and the system is designed to be telecentric at the dies. The beam from each LED passes through the common excitation pupil; this can be accomplished either by use of a full-array diameter field lens or by displacing individual lenslet centers with respect to die centers.

In some embodiments, a system herein comprises 2 arrays of LEDs, for example, green and blue. In other embodiments, an array of LEDs can include LEDs of two different colors, for example, green and blue. In yet other embodiments, any array of LEDs can include LEDs of more than two different colors. With distance, temperature can degrade LED signal, especially for green LEDs. Temperature reduction maximizes radiance form LED and can extend the time of which the well can be imaged with each excitation. Temperature control as provided herein also reduces signal variance and improves measurements.

Figure 11:
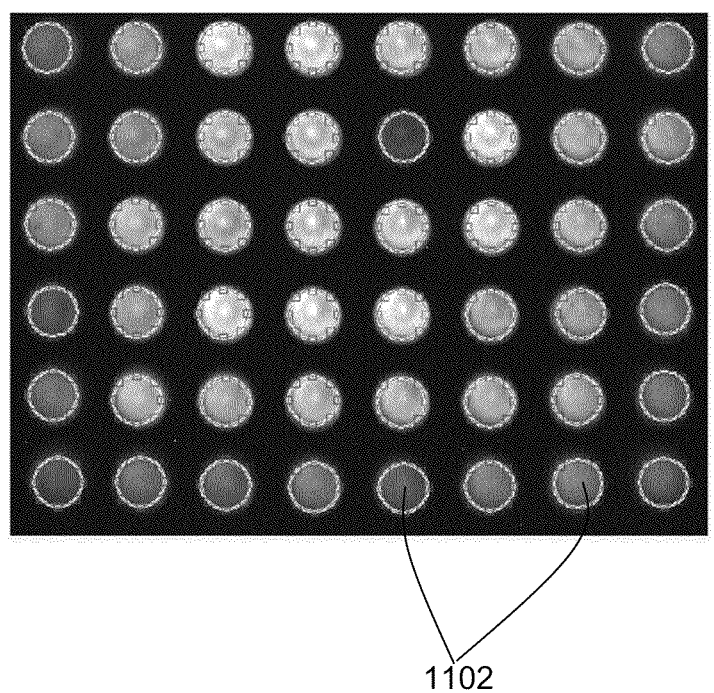
FIG. 11 illustrates a sample image from a 48-well sample plate as excited and detected using an optical system as described herein

FIG. 11 illustrates a sample image from a 48-well sample plate, including well images 1102, as excited and detected using an optical system as described herein. Each well is individually excited and detected using the detector of the optical system.

Figure 12:
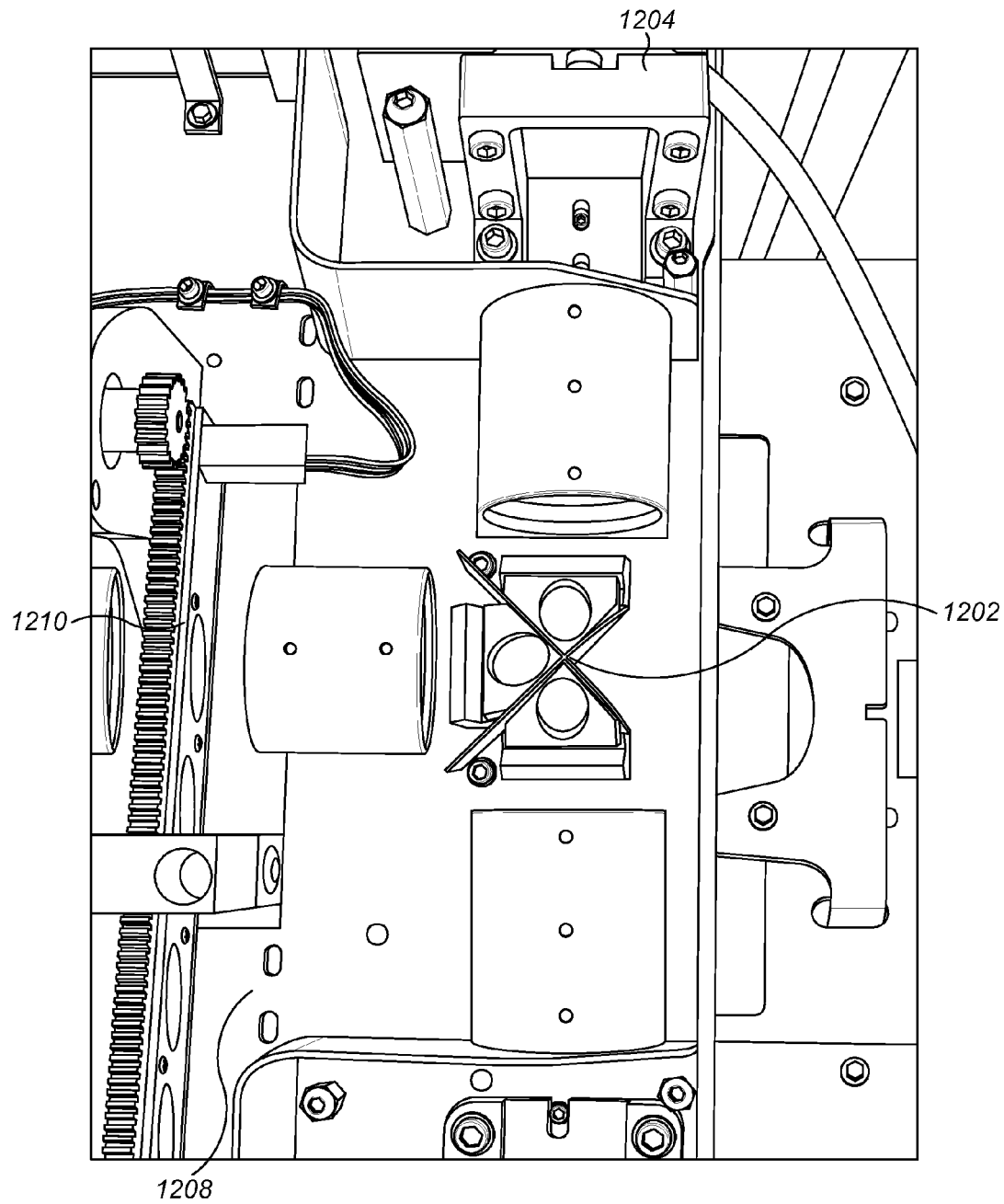
FIG. 12 illustrates an exemplary optical assembly as described herein comprising a multifunction mirror.

FIG. 12 illustrates an example optical assembly as described herein comprising a multifunction mirror 1202. In the example embodiment of FIG. 12, both the excitation source assembly 1204 and the detection assembly are in the same plane. The excitation source assembly, the detection assembly, and the multifunction mirror are mounted on an optical system baseplate 1208. Also demonstrated are optical filters 1210 in the detection optical path that can be moved to change the filter wavelength in the detection optical path.

Figure 13:
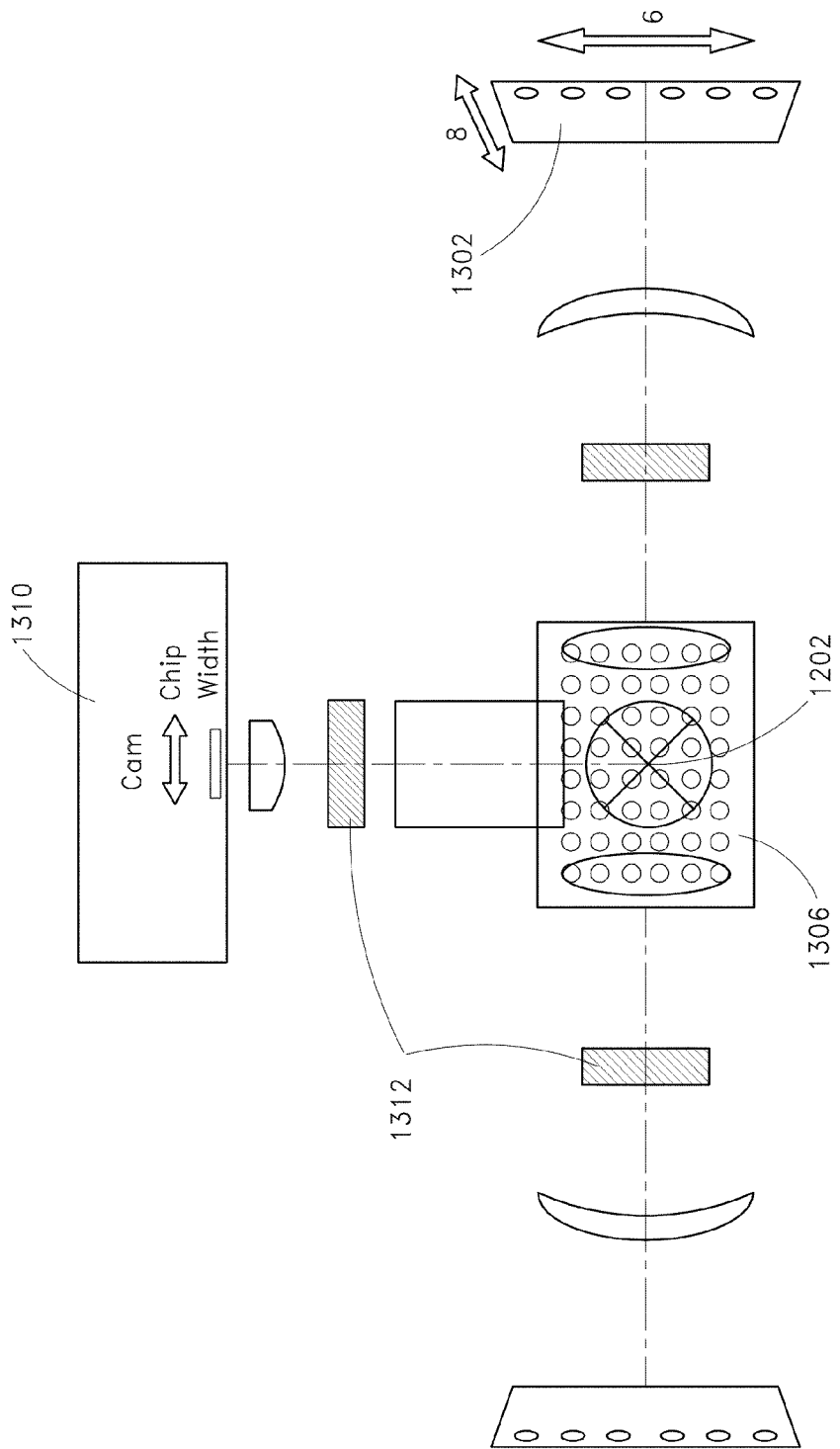
FIG. 13 shows a top view of the optical system over the sample plate.

FIG. 13 shows a top view of the optical system over the sample plate. For example in FIG. 13, the optical system comprises two LED arrays 1302 as described herein that can simultaneously or sequentially excite the samples in the thermal block by directing the energy through the multifunction mirror 1202. The emission from the sample plate on sample block 1306 is directed back through the multifunction mirror 1202 and to the detector 1310 which is in the same plane and mounted on the sample optical plate as the LED arrays 1302 (e.g., the optical baseplate 1208 of FIG. 12). Filters 1312 can be included in the excitation and/or emission paths, as illustrated in FIG. 13.

Figure 14:
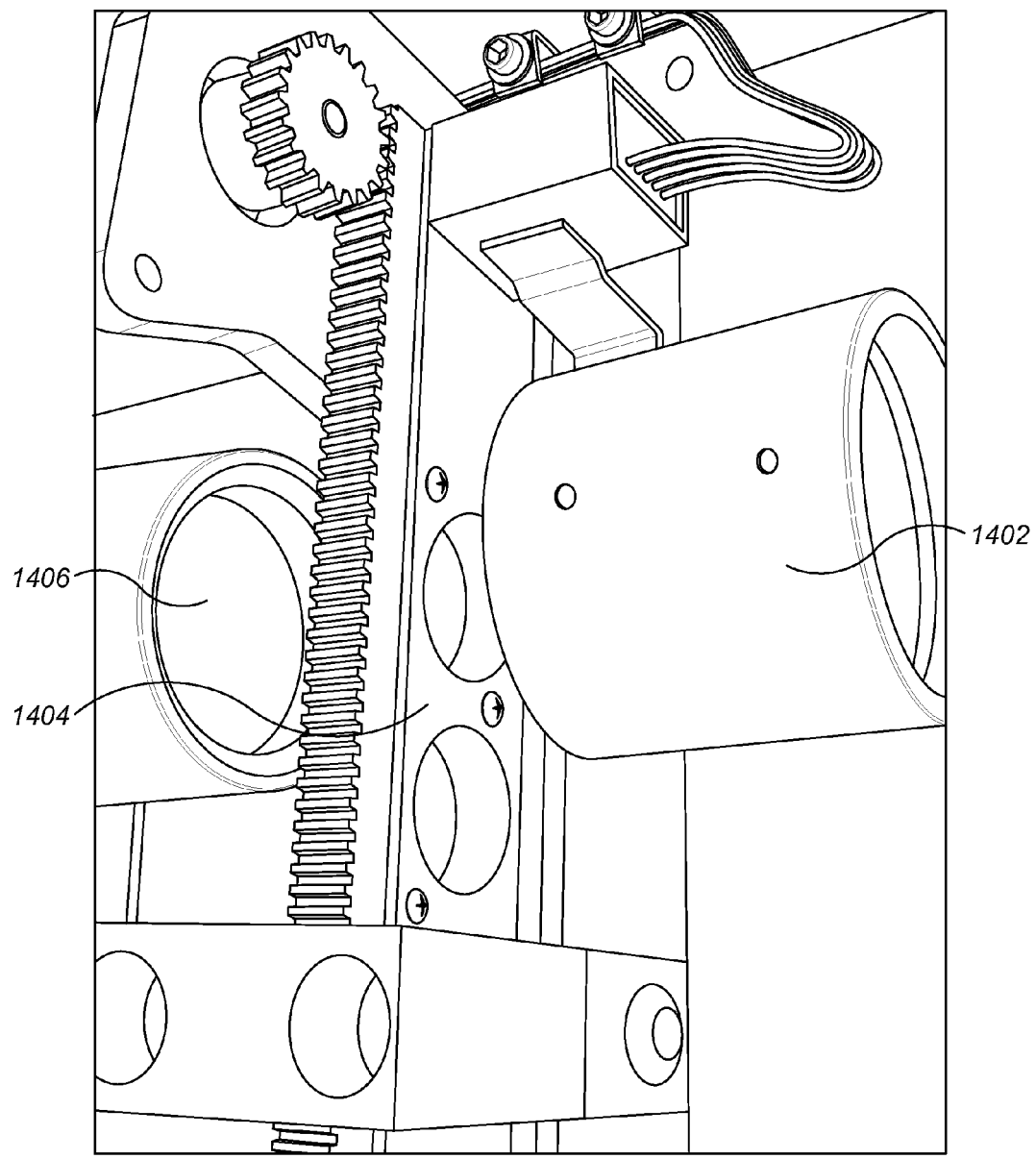
FIG. 14 demonstrates the detection optical path of the optical assembly.

FIG. 14 demonstrates the detection optical path of the optical assembly. In the example embodiment, the detection optical path travels from the multifunction mirror through the detection optics 1402, through a detection optical filter 1404, and to the detector 1406. In an embodiment, the detector 1406 is a CCD camera.

Figure 15:
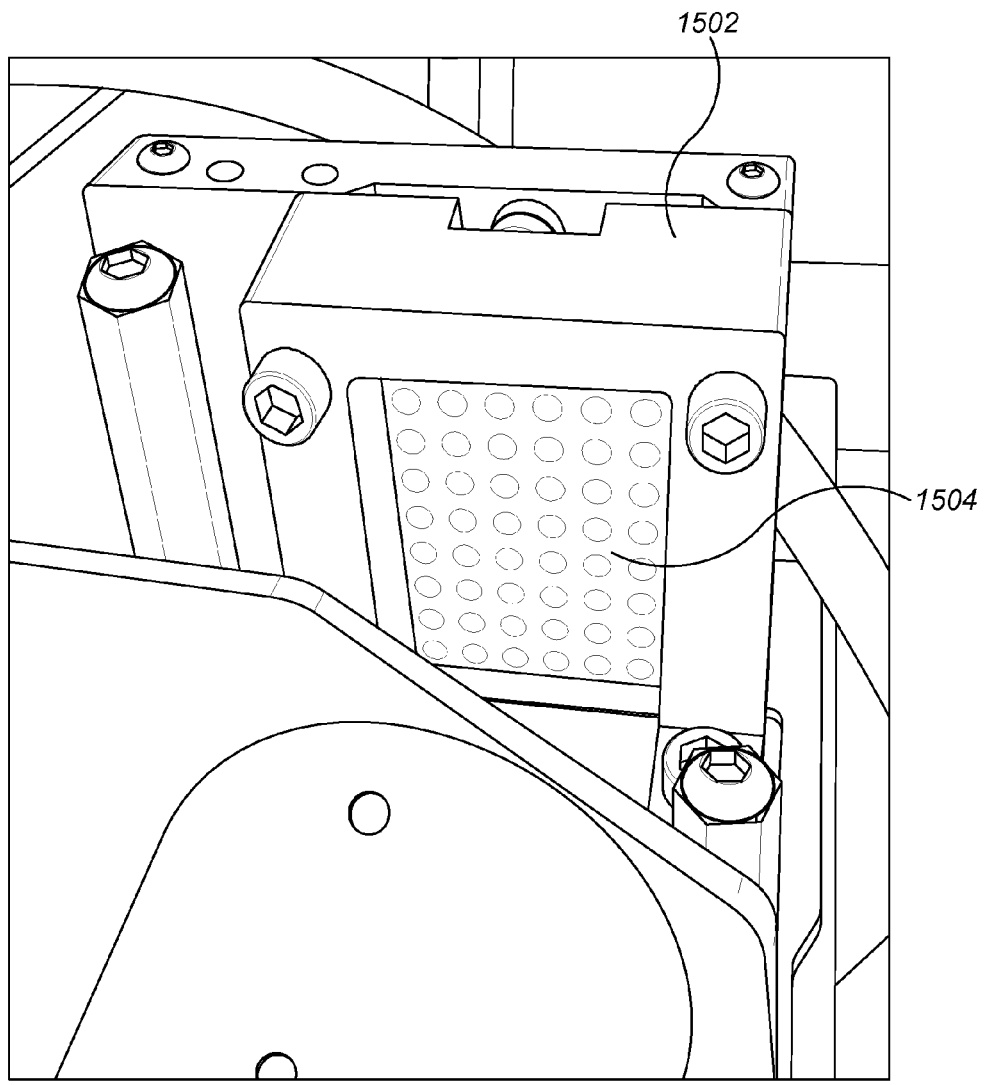
FIG. 15 illustrates an excitation source assembly as described herein. For example, the assembly can comprise an LED array.

FIG. 15 illustrates an excitation source assembly 1502 as described herein. For example, the excitation source assembly 1502 can comprise an LED array. In an embodiment the LED array has the same number of LED sources as there are wells in a sample plate. In another embodiment, the LED array has a different number of LEDs to the number of wells in a sample plate. For example, two or more LEDs can correspond to an individual sample plate. As another example, one LED can provide light to two or more sample plates. In an embodiment, an LED array herein has 48 LEDs. In an embodiment, a sample plate has 48 wells. As demonstrated in FIG. 15, the excitation source assembly can comprise a lenslet array 1504 corresponding to the LED array.

Figure 16:
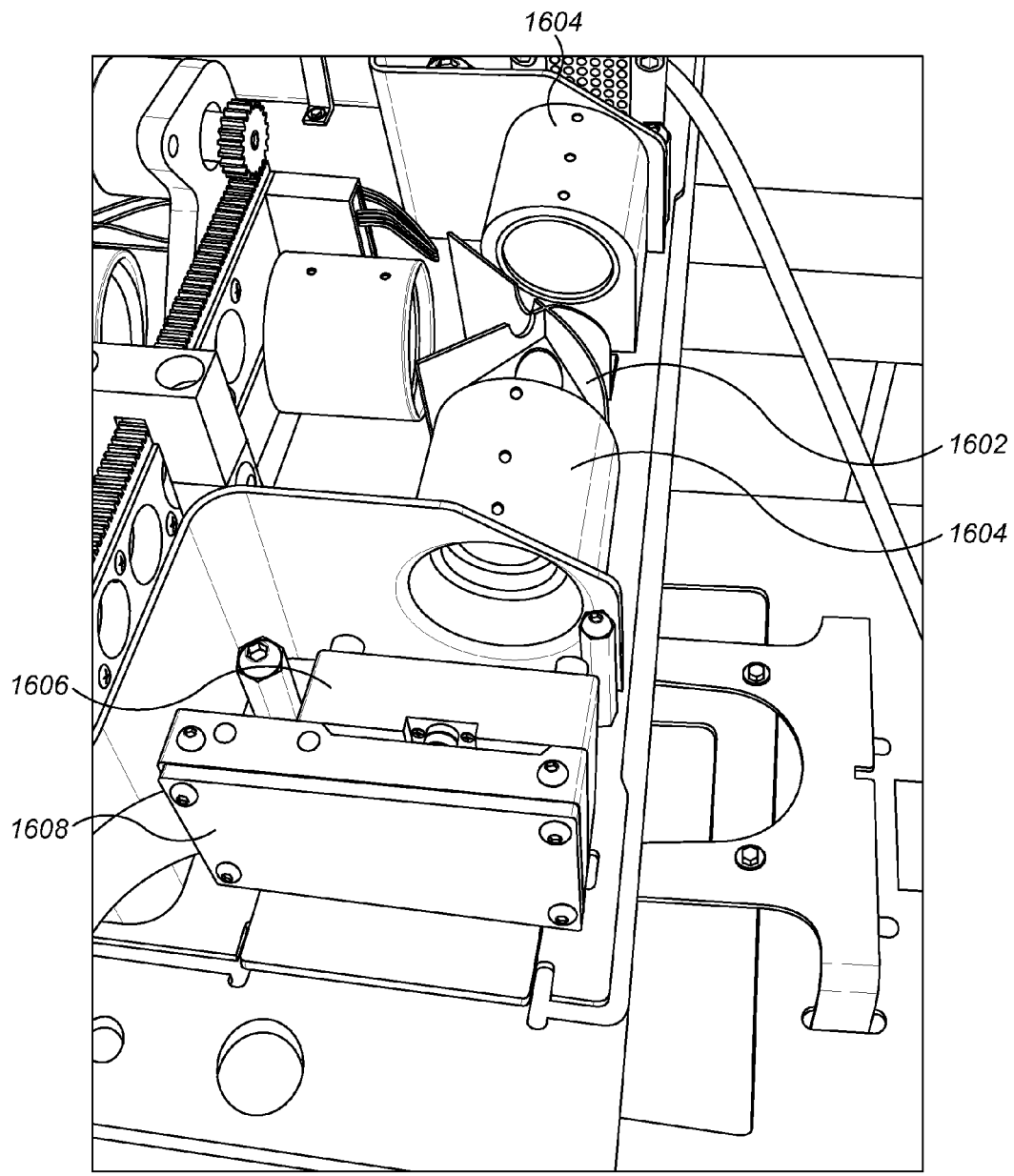
FIG. 16 illustrates an exemplary optical assembly as described herein comprising a multifunction mirror, excitation optics, and an excitation source assembly.

FIG. 16 illustrates an example optical assembly as described herein comprising a multifunction mirror 1602, excitation optics 1604, and an excitation source assembly 1606. In an embodiment, the excitation source assembly 1606 comprises a lens array, an LED array, and backplate 1608 on which the LED array is mounted. Using this configuration, the LED array can be cooled or temperature regulated by regulating the temperature of the backplate 1608. As demonstrated in FIG. 16, both the excitation optical path and the detection optical path are in the same plane. In many embodiments, the optical path plane is parallel to the top surface of the thermal block.

Figure 17:
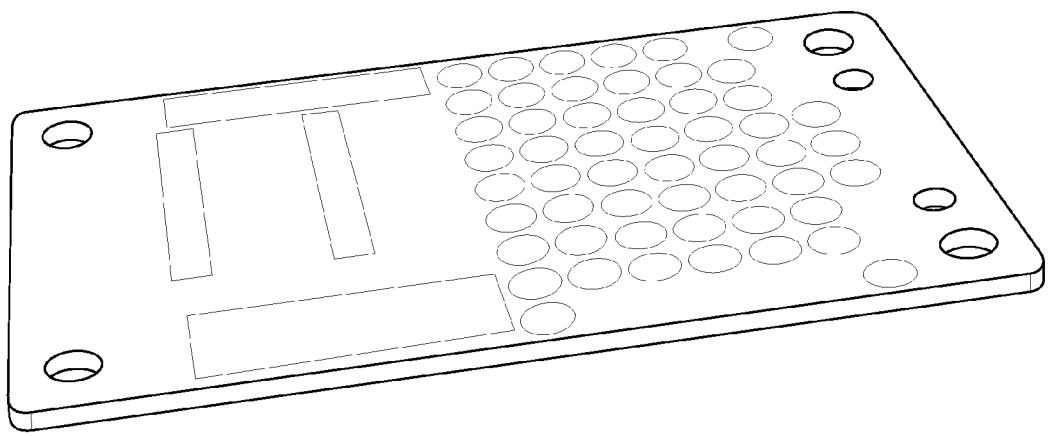
FIG. 17 illustrates an excitation source board on which an array of LEDs can be mounted.

FIG. 17 illustrates an excitation source board 1702 on which an array of LEDs can be mounted. Each LED is separately wired to the control board and can be controlled individually by a computer system. In some instances, each of the LEDs can be programmed to emit different amounts of energy. For example, if one well fluoresces more than another well, the excitation energy from the LED corresponding to that well can be lowered to more easily compare the samples between each well.

In some instances, an excitation source is a flood light, for example, a 100 watt halogen lamp. The light source can provide light at selective wavelengths, coherent or incoherent. A mechanical or electronic shutter can be used for blocking the source beam of the excitation source for obtaining dark data. The type of light source can also be a LED, projection lamp, or a laser, with appropriate optical elements.

In some instances, an excitation source can be used to provide excitation beams to irradiate a sample solution containing one or more dyes. For example, two or more excitation beams having the same or different wavelength emissions can be used such that each excitation beam excites a different respective dye in the sample. The excitation beam can be aimed from the light source directly at the sample, through a wall of a sample container containing the sample, or can be conveyed by various optical systems to the sample. An optical system can include one or more of, for example, a mirror, a beam splitter, a fiber optic, a light guide, or combinations thereof.

According to various embodiments, excitation beams emitted from the light source can diverge from the light source at an angle of divergence. The angle of divergence can be, for example, from about 5° to about 75° or more. The angle of divergence can be substantially wide, for example, greater than 45°, yet can be efficiently focused by use of a lens, such as a focusing lens.

One or more filters, for example, a bandpass filter, can be used with a light source to control the wavelength of an excitation beam. One or more filters can be used to control the wavelength of an emission beam emitted from an excited or other luminescent marker. One or more excitation filters can be associated with a light source to form the excitation beam. One or more filters can be located between the one or more light sources and a sample. One or more emission filters can be associated with an emission beam from an excited dye. One or more filters can be located between the sample and one or more emission beam detectors. According to various embodiments, optics in both the detection and excitation optical paths can include optical filters. Example filters can be conventional optical bandpass filters utilizing optical interference films, each having a bandpass at a frequency optimum either for excitation of the fluorescent dye or its emission. Each filter can have very high attenuation for the other (nonbandpass) frequency, in order to prevent "ghost" images from reflected and stray light. For SYBR Green dye, for example, the excitation filter bandpass wavelength can center around 485 nm, and the emission filter bandpass wavelength can center around 555 nm. The beam splitter can transition from reflection to transmission between these two, for example about 510 nm, so that light less than this wavelength can be reflected and higher wavelength light can be passed through.

According to various embodiments, the excitation source can be a Light Emitting Diode (LED). The LED can be, for example, an Organic Light Emitting Diode (OLED), a Thin Film Electroluminescent Device (TFELD), or a Quantum dot based inorganic organic LED. The LED can include a phosphorescent OLED (PHOLED). As used herein, the terms excitation source and light source are used interchangeably.

Figure 18:
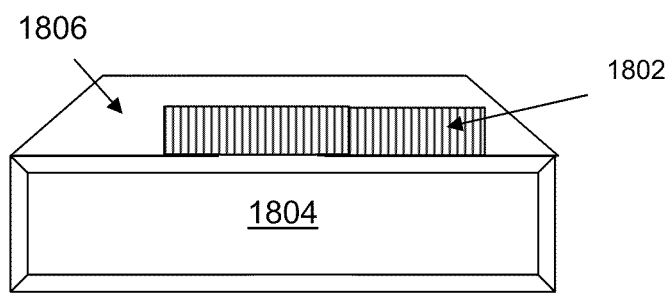
FIG. 18 illustrates an exemplary LED as can be incorporated into a system of the invention.

FIG. 18 illustrates an example LED 1802 as can be incorporated into a system of the invention. The LED 1802 is mounted on an aluminum substrate 1804. The surface of the LED 1802 is coated with epoxy 1806 or another polymer material to protect the diode. Because the aluminum is thermally conductive, the LED 1802 can be cooled or temperature regulated through by cooling or regulating the aluminum substrate 1804.

In some instances, a light source can contain one Light Emitting Diode (LED) or an array of LEDs. According to various embodiments, each LED can be a high power LED that can emit greater than or equal to about 1 mW of excitation energy. In various embodiments, a high power LED can emit at least about 5 mW of excitation energy. In various embodiments wherein the LED or array of LEDs can emit, for example, at least about 50 mW of excitation energy, a cooling device such as, but not limited to, a heat sink or fan can be used with the LED. An array of high-powered LEDs can be used that draws, for example, about 10 watts of energy or less or about 10 watts of energy or more. The total power draw can depend on the power of each LED and the number of LEDs in the array. The use of an LED array can result in a significant reduction in power requirement over other light sources, such as, for example, a 75 watt halogen light source or a 150 watt halogen light source. Example LED array sources are available. In some instances, LED light sources can use about 1 microwatt of power or less, for example, about 1 mW, about 5 mW, about 25 mW, about 50 mW, about 100 mW, about 500 mW about 1 W, about 5 W, about 50 W, or about 100 W or more, individually or when in used in an array. In some instances, the LED light sources use about 1 microwatt to about 100 W of power.

In some embodiments, the optical assembly can be mounted over the thermal block containing the sample plate. In order to access the sample plate when it is in the device, a movable lid (e.g., a hinged lid) comprising a heated lid for the sample plate can be moved without moving the optical assembly or the thermal assembly to access the sample plate. In some instances, the movable lid is positioned to move around the optical assembly. In addition, the movable lid can include a heated lid that is configured to mate with the sample plate. The heated lid can be attached to the movable lid by springs or other materials such that when the movable lid is closed, the heated lid presses tightly against the thermal block to improve thermal contact. The heated lid can include an array of holes therethrough aligned with the wells of the sample plate. Each hole can have a diameter about the same as the top diameter of a well.

Above each of the wells, multiple lenses or a single lens can be positioned such that its focal point is directs energy into each of the well. In some instances, the lens above the sample plate can be a telecentric optical system, a pixilated lens, or preferably a Fresnel lens. In some embodiments, the lens above the wells is incorporated into the movable lid.

Figure 19:
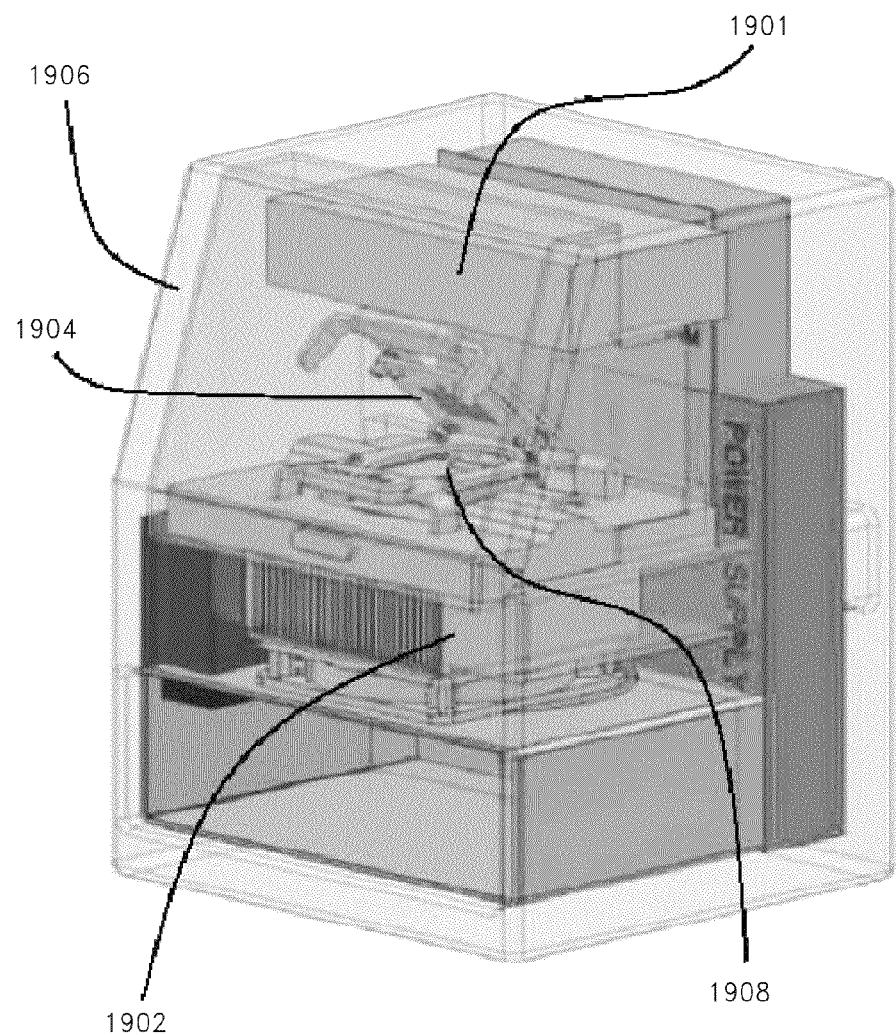
FIG. 19 shows an exemplary thermal cycling device with optical system as described herein.

FIG. 19 shows an example thermal cycling device with optical system as described herein. The cover of the device covers the entire device and can seal the thermal block area for protection while the assay is being run. As shown in FIG. 19, the optical assembly 1901 is mounted above the thermal block and is in a fixed position relative to the thermal assembly 1902. The heated lid 1904 is attached to the movable lid 1906, such that when the movable lid 1906 is open, the heated lid 1904 is not in contact with the sample plate 1908 and allows for placement and removal of the sample plate 1908 from the device. When the movable lid 1906 is closed, the heated lid 1904 is configured to couple with the sample plate 1908. The movable lid 1906 can move independently from the rest of the system, such that it is the only moving part of the system (along with its components such as the heated lid 1904). In another embodiment, the movable lid 1906 (and its components) and a detection filter assembly are the only moving parts of the system.

Figure 20:
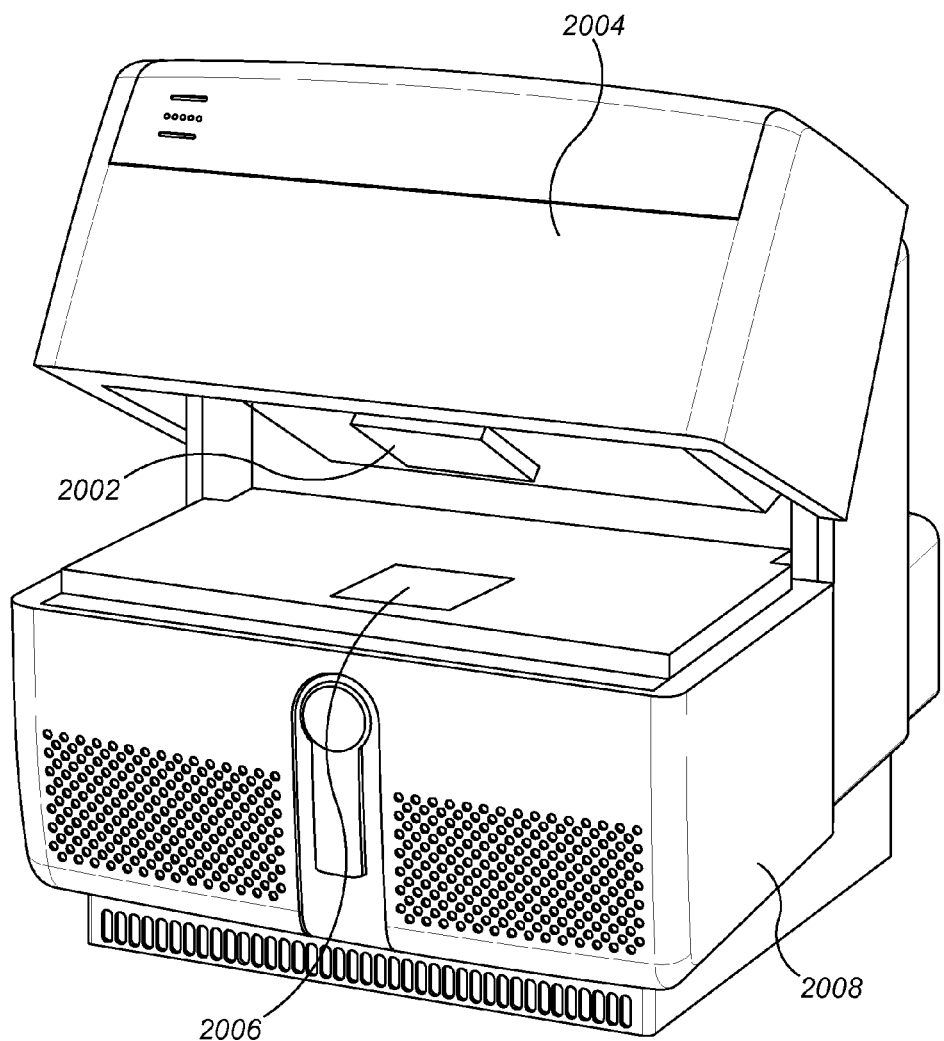
FIG. 20 demonstrates an exemplary thermal cycling device with optical system as described herein with the hinged lid open.

FIG. 20 demonstrates an example thermal cycling device with optical system as described herein with the movable lid open. The heated lid 2002 is visible within the movable lid 2004 and is configured to couple with the sample plate mounted on the thermal assembly 2006. The optical assembly remains in a fixed position relative to the base 2008 of the device.

Figure 21:
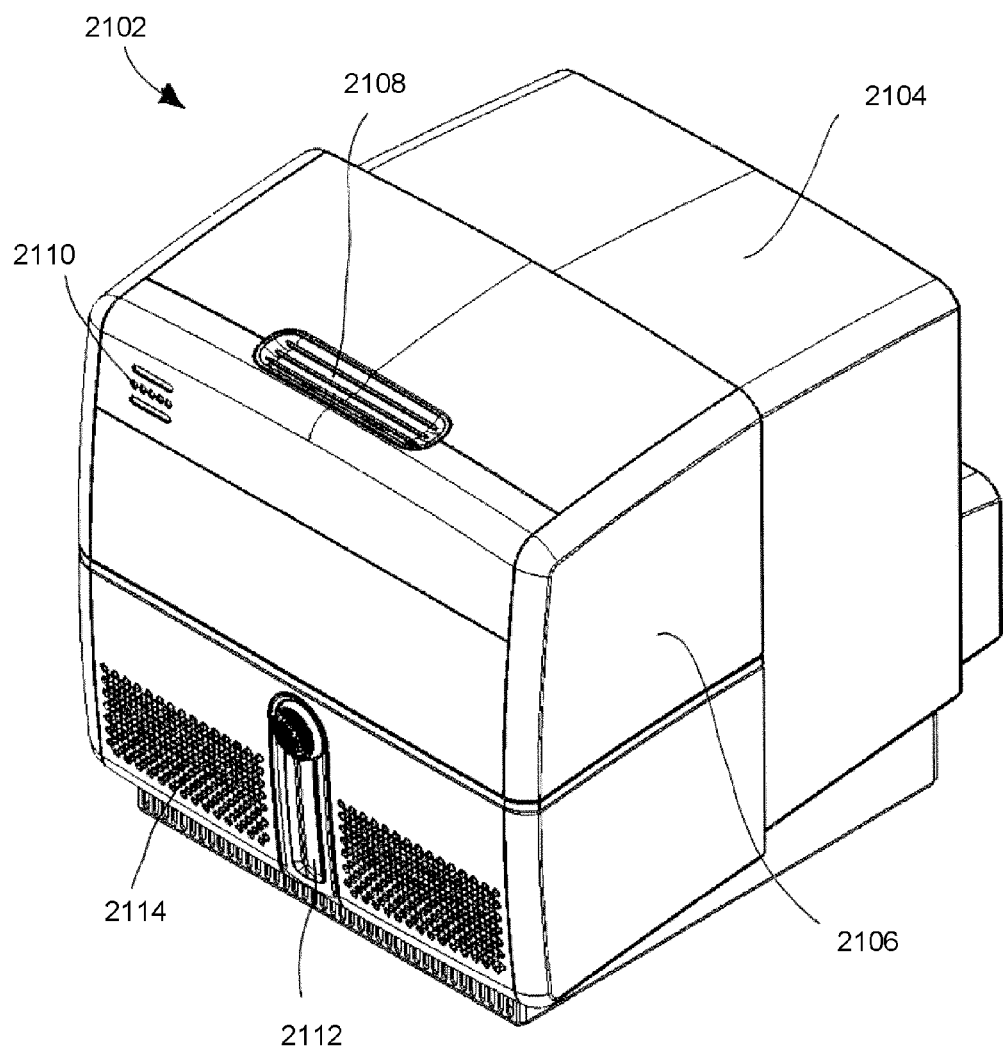
FIG. 21 is a planar view of an exemplary device as described herein.

FIG. 21 illustrates an example device 2102 as described herein. The device body 2104 comprises a movable lid 2106 comprising a grip 2108 and indicator lights 2110, a latch 2112, and cooling vents 2114. The movable lid 2106 opens to provide access to the thermal assembly and to allow a sample holder to be placed within the device 2102. The movable lid 2106 travels over the stationary optical system. In this manner, the optical system is in a fixed position as compared to the thermal assembly and does not move. The movable lid 2106 can also comprise a heated lid that couple to the thermal block to prevent condensation on the sample holder during thermal cycling. In some instances, the movable lid 2106 comprises a lid compression plate that couples with the compression plate on a thermal assembly to provide pressure to couple the heated lid to the sample holder. Cooling portals are also provided for the thermal assembly.

Figure 22:
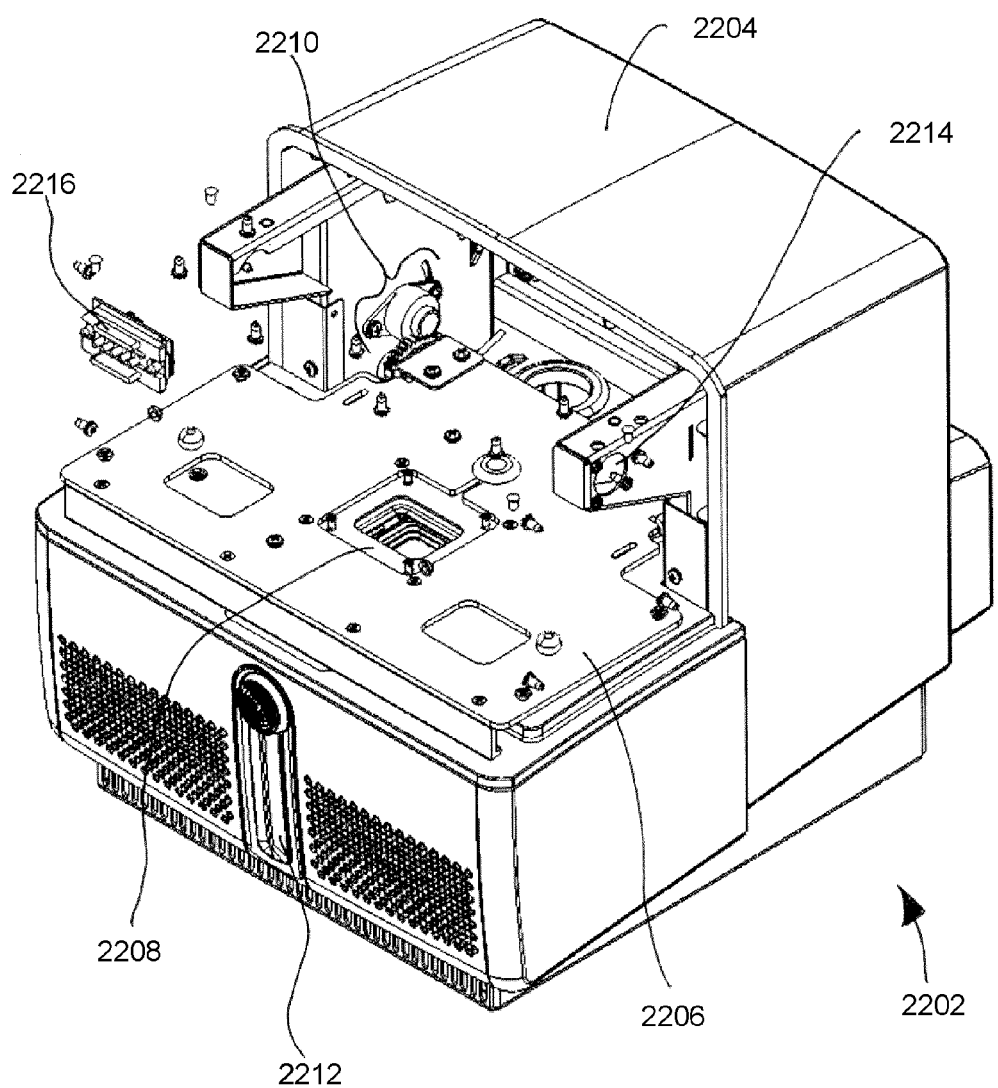
FIG. 22 illustrates an exemplary device as described herein comprising a device body and not displaying the cover to the hinged lid.

FIG. 22 illustrates an example device 2202 as described herein comprising a device body 2204 and not displaying the cover to the movable lid. The movable lid plate 2206 is displayed in FIG. 22. The movable lid plate 2206 comprises a holder 2208 for the heated lid that couples with a sample holder. Also displayed in FIG. 22 is a lid hinge 2210 for the movable lid. In some instances, the lid hinge 2210 is spring loaded. In some instances, the lid hinge 2210 is motorized. In some instances, the lid hinge 2210 is manually powered. The latch 2212 of the body 2204 is used to secure and release the movable lid. Also demonstrated in FIG. 22 is a fan portal 2214 for mounting a cooling fan that cools the excitation source assembly of the optical assembly through the cooling portal. Further illustrated are indicator lights 2216.

Figure 23:
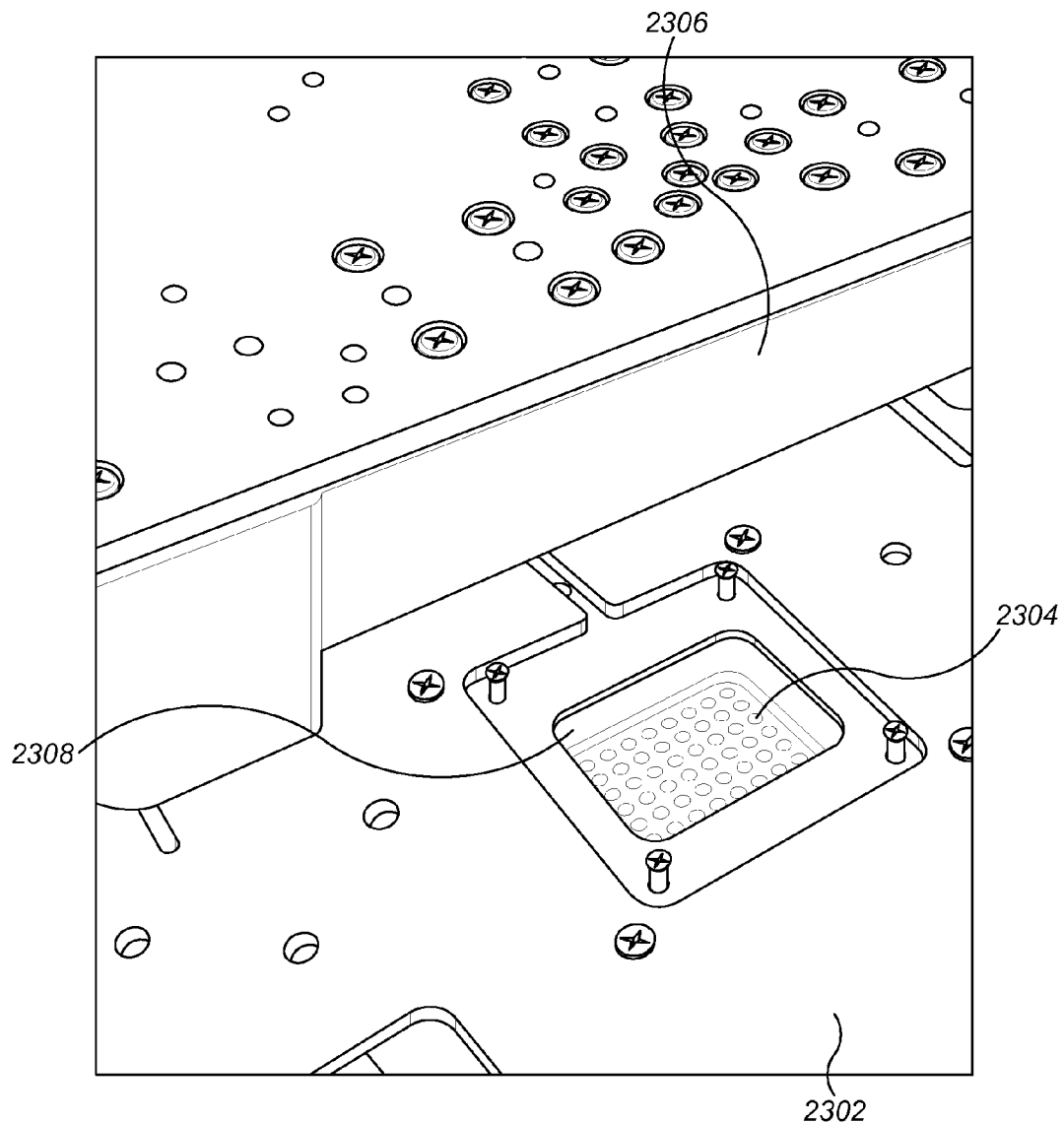
FIG. 23 illustrates a hinged lid plate that can be coupled with a hinged lid that covers the optical assembly.

FIG. 23 illustrates a movable lid plate 2302 that can be coupled with a heated lid 2304 that covers the optical assembly 2306. In many embodiments, the optical assembly 2306 and the thermal assembly are both stationary and the heated lid 2304, which comprises a cover for the sample plate, and a Fresnel lens 2308, can move over the optical assembly and can function to couple the cover to the sample plate of the thermal assembly.

Figure 24:
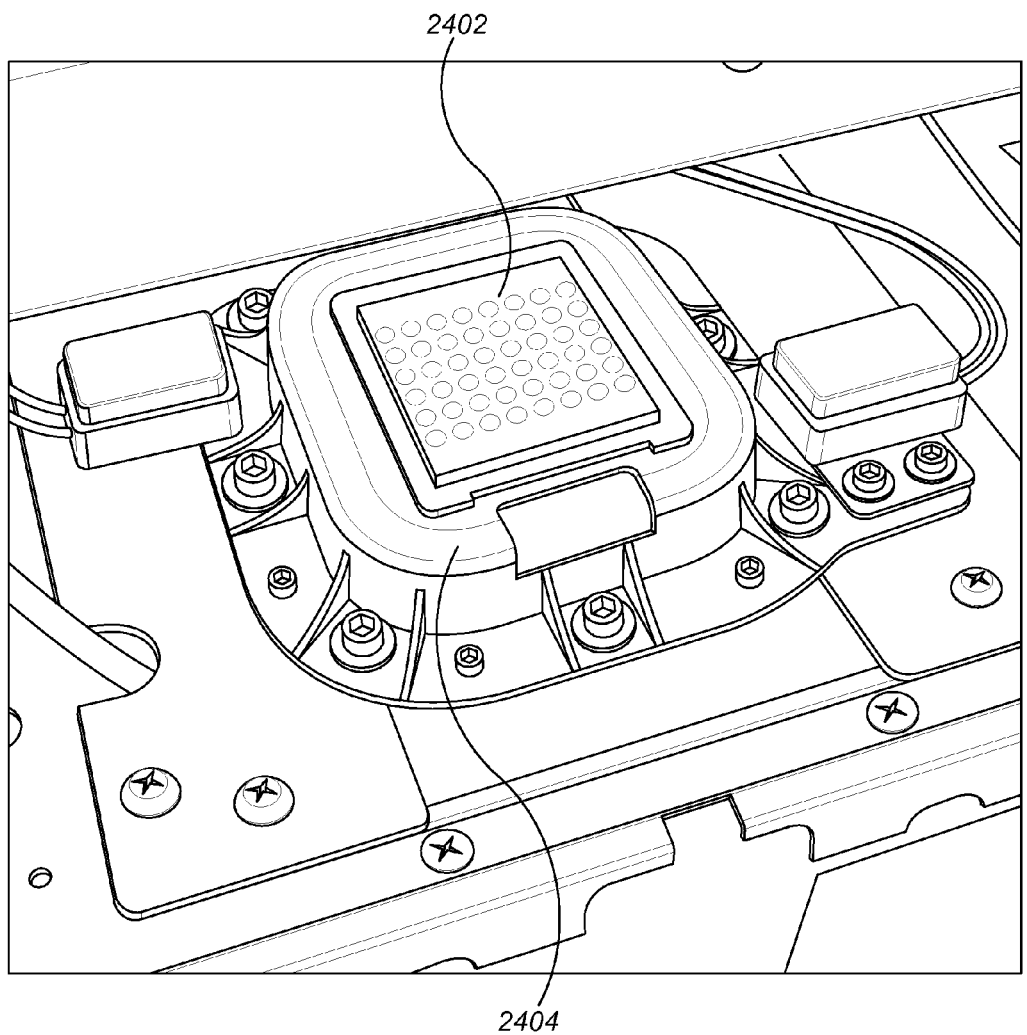
FIG. 24 demonstrates a thermal block and a compression plate of a system as described herein.

FIG. 24 demonstrates a thermal block 2402 and a compression plate 2404 of a system as described herein. The compression plate 2404 has an aperture to provide access to the thermal block 2402 and is configured to receive a cover or heated cover for the thermal block 2402. The compression plate 2404 can couple with the heated cover to provide close or complete thermal contact.

Figure 25:
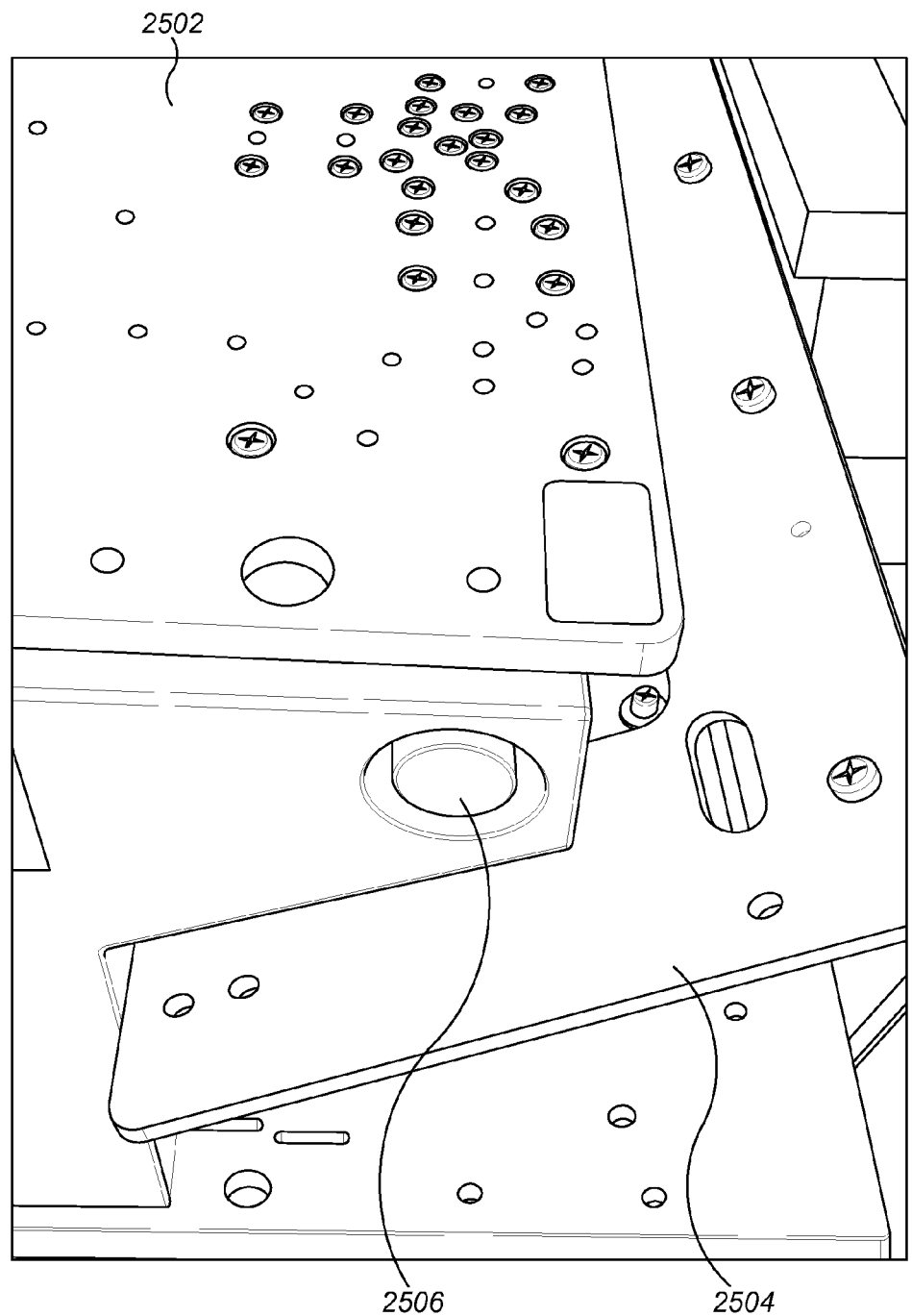
FIG. 25 displays a system herein comprising an optical assembly and a hinged lid plate.

FIG. 25 displays a system herein comprising an optical assembly 2502 and a movable lid plate 2504. The movable lid is not shown. In the example of FIG. 25, the optical assembly 2502 comprises a fan 2506 to provide cooling for the excitation source. For example, if the excitation source is an LED array mounted on an aluminum backplate as described herein, the fan 2506 can cool the LED array.

Any combination of features of the optical systems described herein can be implemented in connection with a thermal assembly. For example, a thermal assembly can include a thermal block including the sample plate. Such an example system can also include: (a) two excitation source assemblies positioned in the excitation optical path, wherein an excitation source assembly comprises one light emitting diode (LED) corresponding to each well on the sample plate;

(b) a multifunction mirror positioned in the excitation optical path to direct excitation energy from each LED to the corresponding well of the sample plate and wherein the multifunction mirror is further positioned in the detection optical path to direct fluorescence emission from the sample plate to a detector; (c) two sets of excitation optics positioned in the excitation optical path, a set of excitation optics comprising an excitation filter and two lenses, optionally, wherein the excitation filter is positioned between the two lenses; (d) a detector positioned in the detection optical path to detect the fluorescent emission that is directed from the multifunctional mirror; and (e) an emission filter slide positioned in the detection optical path between the multifunction mirror and the detector, wherein the emission filter slide comprises at least one emission filter. Moreover, in some instances, the thermal block of this example system can include a liquid composition. The liquid composition can be used to heat and cool samples to a substantially uniform temperature, for example, as described in U.S. patent application Ser. No. 12/753,308, filed Apr. 2, 2010, the entire disclosure of which is hereby incorporated by reference.

In some cases, the system according to certain embodiments also comprises a thermal control unit or a thermal cycler to which the sample vessels in the multi-well plate can mate. The optical systems described herein can be advantageous for measuring the state of reactions within the reaction vessels during and between reaction steps and cycles without having to remove the samples from the thermal cycling element. For example, the system can be used to measure polynucleotide amplification such as polymerase chain reaction (PCR) and real-time polymerase chain reaction (RT-PCR) amplifications.

In embodiments described herein, the multiple temperature cycles correspond to multiple cycles of nucleic acid amplification. Nucleic acid amplification can comprise real-time PCR. For example, an apparatus or system according to certain embodiments can also be referred to as a thermal cycler. Such a thermal cycler can include any combination of features described in U.S. patent application Ser. No. 12/753,308.

As described herein, a thermal block can include a liquid composition that can provide thermal contact between the heater and the sample holder, and provide uniform heat transfer. As a result, the temperatures of the samples within a sample holder can be substantially uniform. The combination of rapid temperature ramp rates and uniformity of temperature decreases non-specific hybridization and significantly increases the specificity (for example, signal-to-noise ratio) of amplification in PCR within individual wells as well as across multiple wells located in the same heat block (or reservoir). In another embodiment, the sample holder, alone or in combination with the apparatus, emits substantially all of a signal generated therein out through a discrete portion of the sample holder, for example, the top of the holder, whereby the emitted light can be collected by an optical assembly. In yet another embodiment a light detector detects substantially all of the light emitted from a sample holder. In certain embodiments the reservoir is highly reflective and reflects light transmitted through the walls of a transparent sample holder back into the sample holder. In this way, a greater proportion of a light signal generated inside the sample holder is emitted from a discrete portion of the sample holder, whereby it can be collected by the optical assembly. In an example, collecting light from a discrete location of the holder can eliminate the necessity of removing the holder from the heat block when performing real-time PCR. Accordingly, the apparatus herein is particularly adapted for performing PCR (polymerase chain reaction), reverse transcription PCR and real-time PCR. In one embodiment an apparatus comprising a reservoir comprising a liquid composition is powered by a battery or AC or DC current.

In addition to providing thermal cycling for PCR, an apparatus herein can be used widely in the field of biotechnology and chemistry as is discussed herein. The use of a liquid composition as described can result in a more uniform heat transfer and more rapid heating and cooling cycles than solid metal heat blocks, which in an example, can lead to lower error rates by DNA polymerases. Further, error rates may be decreased during long amplifications, SNP identification and sequencing reactions, because of the enhanced thermal uniformity.

In some instances, the heater is a thermoelectric device. In other instances, the heater is a resistive device. An apparatus herein can also comprise a cooler. In some instances, the heater and the cooler are the same device, for example, a Peltier device.

A variety of heaters and coolers are known to a practitioner in the art. In one embodiment, a heater is a Peltier device or a resistive heater. In an embodiment, the thermal block is in thermal contact with a Peltier-effect thermoelectric device. In an alternative embodiment, the heater may be provided by extending a tube into the thermal block through which hot or cold fluids can be pumped. In alternative embodiments, the thermal block can be fitted with a heating and/or cooling coil, or with an electrical resistance heater arranged to prevent edge effects.

Peltier devices or elements, also known as thermoelectric (TE) modules, are small solid-state devices can function as heat pumps. A typical Peltier unit is a few millimeters thick by a few millimeters to a few centimeters in a square or rectangular shape. It is a sandwich formed by two ceramic plates with an array of small Bismuth Telluride (Bi2Te3) cubes ("couples") in between. When a DC current is applied heat is moved from one side of the device to the other where it can be removed by a heat sink. The "cold" side may be attached to a heat sink. If the current is reversed the device changes the direction in which the heat is moved. Peltier devices lack moving parts, do not require refrigerant, do not produce noise or vibration, are small in size, have a long life, and are capable of precision temperature control. Temperature control may be provided by using a temperature sensor feedback (such as a thermistor or a solid-state sensor) and a closed-loop control circuit, which may be based on a general purpose programmable computer.

In another embodiment the thermal cycler may further comprise an electric resistance heater and a Peltier element used in combination to obtain the required speed of the temperature changes in the thermal block and the required precision and homogeneity of the temperature distribution.

A heater as described herein may also comprise a heat sink as is known to one skilled in the art. In one embodiment, a heat sink is a Peltier device, a refrigerator, an evaporative cooler, a heat pipe, a heat pump, or a phase change material. In one embodiment, the heat sink is a thermoelectric device such as a Peltier device. The heat sink may also be a heat pipe, which is a sealed vacuum vessel with an inner wick which serves to transfer heat by the evaporation and condensation of a fluid. Heat pipes which are suitable for use in the invention are disclosed, for example in WO 01/51209, U.S. Pat. No. 4,950,608, and U.S. Pat. No. 4,387,762. Similarly suitable devices are produced by the company Thermacore (Lancester, USA) and sold under the trade name Therma-Base™. Additional devices for use as heat sinks are also described in U.S. Pat. No. 5,161,609 and U.S. Pat. No. 5,819,842.

In an alternative embodiment, a heater and sometimes the reservoir is designed to maintain different temperatures in different zones of the reservoir wells. This can allow different sample wells in different zones to be cycled at different temperatures simultaneously. In one embodiment the liquid metal or thermally conductive fluid heat block is a capable of maintaining a temperature gradient across 2, 3, 4, 5, 6 or more zones. In one embodiment temperature gradients in excess of 0.1° C. to 20° C. across the reservoir can be achieved. In some embodiments the heat block will contain internal baffles or insulated walls which act to separate different zones of the liquid composition from other zones. Each zone may further comprise an individual fluid stirrer. Further each zone of the heat block may comprise individual heating and/or cooling elements such as a heat conduction element (wires, tubes), thin foil type heater, Peltier elements or cooling units.

As described herein, the sample holder can be a multiwell plate. In some instances, the multiwell plate has 16, 24, 48, 96, 384 or more sample wells. In some of these instances, an array of light sources, such as LEDs, has 16, 24, 48, 96, 384 or more corresponding light sources. In some instances, the multiwell plate is a standard microwell plate for biological analysis. For example, the multiwell plate can be plate used for PCR. In an embodiment, the multiwell plate has of 48 sample wells. The apparatus described herein can function to keep the temperature of the samples within each of the sample wells of a multiwell plate within ±0.3° C. In other embodiments, the sample holder can be sample tubes, such as Eppendorf tubes.

As described herein, a sample holder can be reaction vessels of a variety of shapes and configurations. In an embodiment sample holder can be used to contain reaction mixtures, such as PCR reaction mixtures, reverse transcription reaction mixtures, real-time PCR reaction mixtures, or any other reaction mixture which requires heating, cooling or a stable uniform temperature. In one embodiment the sample holder is round or tubular shaped vessels. In an alternative embodiment the sample holder is oval vessels. In another embodiment the sample holder is rectangular or square shaped vessels. Any of the preceding embodiments may further employ a tapered, rounded or flat bottom. In yet another embodiment the sample holder is capillary tubes, such as clear glass capillary tubes or coated capillary tubes, wherein the coating (for example metal) increases internal reflectivity. In an additional embodiment the sample holder is slides, such as glass slides. In another embodiment the sample holder is sealed at the bottom. In another embodiment the sample holder is coated, at least internally, with a material for preventing an amplicon from sticking to the sample holder walls, such as a fluorinated polymer or BSA.

In one embodiment the sample holder is manufactured and used as individual vessels. In another embodiment the sample holder is a plurality of vessels linked together in a horizontal series comprising a multiple of individual vessels, such as 2, 4, 6, 10, 12, 14 or 16 tubes. In yet another embodiment the sample holder is linked together to form a sheet, plate or tray of vessels designed to fit into the top of the heating block of a thermal cycler so as to occupy some or all available reaction wells. In one embodiment the holder is a microplate comprising at least 6, wells, 12 wells, 24 wells, 36 wells, 48 wells, 54 wells, 60 wells, 66 wells, 72 wells, 78 wells, 84 wells, 90 wells or 96 wells, 144 wells, 192 wells, 384 wells, 768, or 1536 wells.

In one embodiment the sample holder has caps or a cover attached to the open ends of sample wells or vessels. In one embodiment the sample wells or vessels are designed to hold a maximum sample volume, such as 10 ul, 20 ul, 30 ul, 40 ul, 50 ul, 60 ul, 70 ul, 80 ul, 90 ul, 100 ul, 200 ul, 250 ul, 500 ul, 750 ul, 1000 ul, 1500 ul, 2000 ul, 5 mL, or 10 mL.

In some embodiments real-time polymerase chain reactions (PCR) are performed in a sample holder manufactured from materials chosen for their optical clarity and for their known non-interaction with the reactants, such as glass or plastic. In one embodiment the sample holder is designed so that light can enter and leave through the top portion of the sample wells, which may be covered with a material at least partially transparent to light. In one embodiment the sample holder is designed so that light is directed to exit through a single surface, such as the top or bottom.

In other embodiments the sample holder is manufactured from materials that are substantially internally reflective, such as reflective plastic, coated plastic (such as with metal or other reflective substances), coated glass (such as with metal or other reflective substances), doped glass (manufactured with the addition of molecules that increase the reflectivity of the glass), or metal, including but not limited to stainless steel, chromium, or other substantially non-reactive metals.

In an aspect, a method of heating a biological sample comprises: positioning a sample holder containing a biological sample into thermal contact with an apparatus as described herein; and heating the biological sample contained by the sample holder with the apparatus.

In an embodiment, the method comprises performing PCR on the biological sample. The heating can comprises thermally cycling the biological sample between about 50-65° C. and about 90 to 100° C. PCR processes and methods are discussed in further detail herein.

In some instances, an apparatus herein maintains the temperature of a plurality of biological samples when heating. For example, a plurality of biological samples can be heated to 95° C. from 60° C., and within 10 s, each of the biological samples is maintained within ±0.3° C. of each other. In an embodiment, a plurality of biological samples is maintained within ±0.5° C., ±0.4° C., ±0.3° C., ±0.2° C., ±0.1° C., ±0.05° C., or ±0.01° C. of each other. In an embodiment, a plurality of biological samples are brought to a temperature within ±0.5° C., ±0.4° C., ±0.3° C., ±0.2° C., ±0.1° C., ±0.05° C., or ±0.01° C. within 30, 20, 20, 5, 3, 2, 1, or 0.5 s after changing the temperature of the biological samples by more than 5, 10, 20, 30, 40, or 50° C. When changing temperature of biological samples using, for example, thermal cycling, temperature uniformity of a plurality of biological samples can be important for improving the quality of any assay or reaction products.

As described, the sample holder can be a multiwell plate and the wells of the multiwell plate contain the biological sample, wherein the biological sample is a polynucleotide sample.

In some instances, a method herein comprises providing reagents for carrying out PCR, and dyes for detecting the level of amplification to the wells containing the biological sample, thereby creating a reaction mixture.

Heating can comprise cycling the temperature of reaction mixture in the wells to perform multiple amplification cycles. In some instances, each of the amplification cycles comprise an annealing temperature and a denaturing temperature, and wherein the annealing (or denaturing or both) temperature of each amplification cycle varies by less than ±0.3° C.

In some embodiments the uniformity of temperature of the liquid composition and reservoir is regulated by a step of a method herein of circulating the liquid composition in the reservoir. Circulation of the liquid metal or thermally conductive fluid can be created by natural convection or forced convection, such as by the intervention of a device including but not limited to a stir bar and a pump.

In some embodiments a method herein provides a thermal cycling ramp rate at a rate substantially faster than conventional metal heat blocks, such as at a rate of at least 5-50.5° C. per second, including but not limited to a range of at least 10-40° C. per second. In a related embodiment a method and apparatus herein can change temperature at a rate substantially faster than conventional metal heat blocks while maintaining a more uniform temperature across the heat block and/or within a sample within said heat block. In one embodiment the temperature of the biological samples in thermal contact with the heat block can be measured with glass bead thermistors (Betatherm). In another embodiment an infrared camera is used to measure the temperature of the samples. In another embodiment the temperature of the liquid sample is measured with an external probe.

In some instances, a method comprises thermally cycling a biological sample. In some instances, the thermal cycling of a biological sample can occur faster than many current standard thermal cycling devices. In an embodiment, an apparatus described herein comprising a reservoir and a stirring device can heat a PCR reaction from the annealing temperature to the denaturing temperature of the reaction in less than 10, 5, 4, 3, 2, 1, 0.5, 0.2, 0.1, or 0.05 s. In an embodiment, an apparatus described herein comprising a reservoir and a stirring device can cool a PCR reaction from the denaturing temperature to the annealing temperature of the reaction in less than 10, 5, 4, 3, 2, 1, 0.5, 0.2, 0.1, or 0.05 s.

A method herein can also further comprise optically measuring the dyes between or during each of a plurality of amplification cycles to determine the level of amplification.

In an aspect, a method of heating a biological sample as disclosed herein comprises: positioning a sample holder into thermal contact with a heater, wherein the sample holder comprises at least about 16 wells containing a biological sample and is at least 1 cm in width; and heating the biological sample within the sample holder with the heater; wherein the temperature variance of the biological sample between each of the at least about 16 wells is less than ±0.3° C. In some instances, the temperature variance is less than ±0.3° C. within 10 seconds immediately after increasing or decreasing the temperature of the biological sample more than 10° C. per second. In an embodiment, the sample holder is at least 0.1, 0.5, 1, 2, 3, 4, 5, or 10 cm in width. In an embodiment, all the wells are at the same temperature at the same time.

In various embodiments a control assembly is operatively linked to an apparatus or thermal cycler of the invention. Such a control assembly, for example, comprises a programmable computer comprising computer executable logic that functions to operate any aspect of the devices, methods and/or systems of the invention. For example, the control assembly can turn on/off or actuate motors, fans, regulating circuits, stir bars, continuous flow devices and optical assemblies. The control assembly can be programmed to automatically process samples, run multiple PCR cycles, obtain measurements, digitize measurements into data, convert data into charts/graphs and report.

Computers for controlling instrumentation, recording signals, processing and analyzing signals or data can be any of a personal computer (PC), digital computers, a microprocessor based computer, a portable computer, or other type of processing device. Generally, a computer comprises a central processing unit, a storage or memory unit that can record and read information and programs using machine-readable storage media, a communication terminal such as a wired communication device or a wireless communication device, an output device such as a display terminal, and an input device such as a keyboard. The display terminal can be a touch screen display, in which case it can function as both a display device and an input device. Different and/or additional input devices can be present such as a pointing device, such as a mouse or a joystick, and different or additional output devices can be present such as an enunciator, for example a speaker, a second display, or a printer. The computer can run any one of a variety of operating systems, such as for example, any one of several versions of Windows, or of MacOS, or of Unix, or of Linux.

In some embodiments, the control assembly executes the necessary programs to digitize the signals detected and measured from reaction vessels and process the data into a readable form (for example, table, chart, grid, graph or other output known in the art). Such a form can be displayed or recorded electronically or provided in a paper format.

In some embodiments, the control assembly controls regulating circuits linked to the thermal elements so as to regulate/control cycles of temperatures of an apparatus as described herein.

In further embodiments, for example in real-time PCR, the control assembly generates the sampling strobes of the optical assembly, the rate of which is programmed to run automatically. The timing can be adjustable for shining a light sources and operating a detector to detect and measure signals (for example, fluorescence).

In another embodiment an apparatus comprising a control assembly further comprises a means for moving sample vessels into apertures, such as wells in the receptacle of a heat block comprising a liquid composition. In an embodiment said means could be a robotic system comprising motors, pulleys, clamps and other structures necessary for moving sample vessels.

In some aspects of the invention, the devices/systems of the invention are operatively linked to a robotics sample preparation and/or sample processing unit. For example, a control assembly can provide a program to operate automated collection of samples, adding of reagents to collection tubes, processing/extracting nucleic acids from said tubes, optionally transferring samples to new tubes, adding necessary reagents for a subsequent reaction (for example, PCR or sequencing), and transferring samples to a thermal cycler according to the invention.

A system as configured herein can be used for disease diagnosis, drug screening, genotyping individuals, phylogenetic classification, environmental surveillance, parental and forensic identification amongst other uses. Further, nucleic acids can be obtained from any source for experimentation. For example, a test sample can be biological and/or environmental samples. Biological samples may be derived from human, other animals, or plants, body fluid, solid tissue samples, tissue cultures or cells derived therefrom and the progeny thereof, sections or smears prepared from any of these sources, or any other samples suspected to contain the target nucleic acids. Example biological samples are body fluids including but not limited to blood, urine, spinal fluid, cerebrospinal fluid, sinovial fluid, ammoniac fluid, semen, and saliva. Other types of biological sample may include food products and ingredients such as vegetables, dairy items, meat, meat by-products, and waste. Environmental samples are derived from environmental material including but not limited to soil, water, sewage, cosmetic, agricultural, industrial samples, air filter samples, and air conditioning samples.

An apparatus herein can be used in any protocol or experiment that requires either thermal cycling or a heat block that can accurately maintain a uniform temperature. For example said thermal cycler can be used for polymerase chain reaction (PCR), quantitative polymerase chain reaction (qPCR), nucleic acid sequencing, ligase chain polymerase chain reaction (LCR-PCR), reverse transcription PCR reaction (RT-PCR), single base extension reaction (SBE), multiplex single base extension reaction (MSBE), reverse transcription, and nucleic acid ligation.

PCR reaction conditions typically comprise either two or three step cycles. Two step cycles have a denaturation step followed by a hybridization/elongation step. Three step cycles comprise a denaturation step followed by a hybridization step during which the primer hybridizes to the strands of DNA, followed by a separate elongation step. The polymerase reactions are incubated under conditions in which the primers hybridize to the target sequences and are extended by a polymerase. The amplification reaction cycle conditions are selected so that the primers hybridize specifically to the target sequence and are extended.

Successful PCR amplification requires high yield, high selectivity, and a controlled reaction rate at each step. Yield, selectivity, and reaction rate generally depend on the temperature, and optimal temperatures depend on the composition and length of the polynucleotide, enzymes and other components in the reaction system. In addition, different temperatures may be optimal for different steps. Optimal reaction conditions may vary, depending on the target sequence and the composition of the primer. Thermal cyclers may be programmed by selecting temperatures to be maintained, time durations for each cycle, number of cycles, rate of temperature change and the like.

Primers for amplification reactions can be designed according to known algorithms. For example, algorithms implemented in commercially available or custom software can be used to design primers for amplifying desired target sequences. Typically, primers can range from least 12 bases, more often 15, 18, or 20 bases in length but can range up to 50+ bases in length. Primers are typically designed so that all of the primers participating in a particular reaction have melting temperatures that are within at least 5° C., and more typically within 2° C. of each other. Primers are further designed to avoid priming on themselves or each other. Primer concentration should be sufficient to bind to the amount of target sequences that are amplified so as to provide an accurate assessment of the quantity of amplified sequence. Those of skill in the art will recognize that the amount of concentration of primer will vary according to the binding affinity of the primers as well as the quantity of sequence to be bound. Typical primer concentrations will range from 0.01 uM to 0.5 uM.

In one embodiment, an apparatus herein may be used for PCR, either as part of a thermal cycler or as a heat block used to maintain a single temperature. In a typical PCR cycle, a sample comprising a DNA polynucleotide and a PCR reaction cocktail is denatured by treatment in a thermal block at about 90-98° C. for 10-90 seconds. The denatured polynucleotide is then hybridized to oligonucleotide primers by treatment in a thermal block of the invention at a temperature of about 30-65° C. for 1-2 minutes. Chain extension then occurs by the action of a DNA polymerase on the polynucleotide annealed to the oligonucleotide primer. This reaction occurs at a temperature of about 70-75° C. for 30 seconds to 5 minutes in the thermal block. Any desired number of PCR cycles may be carried out depending on variables including but not limited to the amount of the initial DNA polynucleotide, the length of the desired product and primer stringency.

In another embodiment, the PCR cycle comprises denaturation of the DNA polynucleotide at a temperature of 95° C. for about 1 minute. The hybridization of the oligonucleotide to the denatured polynucleotide occurs at a temperature of about 37-65° C. for about one minute. The polymerase reaction is carried out for about one minute at about 72.degree. C. All reactions are carried out in a multiwell plate which is inserted into the wells of a receptacle in a thermal block of the invention. About 30 PCR cycles are performed. The above temperature ranges and the other numbers are not intended to limit the scope of the invention. These ranges are dependant on other factors such as the type of enzyme, the type of container or plate, the type of biological sample, the size of samples, etc. One of ordinary skill in the art will recognize that the temperatures, time durations and cycle number can readily be modified as necessary.

Reverse transcription refers to the process by which mRNA is copied to cDNA by a reverse transcriptase (such as Moloney murine leukemia virus (MMLV) transcriptase avian myeloblastosis virus (AMV) transcriptase or a variant thereof) composed using an oligo dT primer or random oligomers (such as a random hexamer or octamer). In real-time PCR, a reverse transcriptase that has an endo H activity is typically used. This removes the mRNA allowing the second strand of DNA to be formed. Reverse transcription typically occurs as a single step before PCR. In one embodiment the RT reaction is performed in a thermal block of the invention by incubating an RNA sample a transcriptase the necessary buffers and components for about an hour at about 37° C., followed by incubation for about 15 minutes at about 45° C. followed by incubation at about 95° C. The cDNA product is then removed and used as a template for PCR. In an alternative embodiment the RT step is followed sequentially by the PCR step, for example in a one-step PCR protocol. In this embodiment all of the reaction components are present in the sample vessel for the RT step and the PCR step. However, the DNA polymerase is blocked from activity until it is activated by an extended incubation at 95° C. for 5-10 minutes. In one embodiment the DNA polymerase is blocked from activity by the presence of a blocking antibody that is permanently inactivated during the 95° C. incubation step.

In molecular biology, real-time polymerase chain reaction, also called quantitative real time polymerase chain reaction (QRT-PCR) or kinetic polymerase chain reaction, is used to simultaneously quantify and amplify a specific part of a given DNA molecule. It is used to determine whether or not a specific sequence is present in the sample; and if it is present, the number of copies in the sample. It is the real-time version of quantitative polymerase chain reaction (Q-PCR), itself a modification of polymerase chain reaction.

The procedure follows the general pattern of polymerase chain reaction, but the DNA is quantified after each round of amplification; this is the "real-time" aspect of it. In one embodiment the DNA is quantified by the use of fluorescent dyes that intercalate with double-strand DNA. In an alternative embodiment modified DNA oligonucleotide probes that fluoresce when hybridized with a complementary DNA are used to quantify the DNA.

In another embodiment real-time polymerase chain reaction is combined with reverse transcription polymerase chain reaction to quantify low abundance messenger RNA (mRNA), enabling a researcher to quantify relative gene expression at a particular time, or in a particular cell or tissue type.

In certain embodiments, the amplified products are directly visualized with detectable label such as a fluorescent DNA-binding dye. In one embodiment the amplified products are quantified using an intercalating dye, including but not limited to SYBR green, SYBR blue, DAPI, propidium iodine, Hoeste, SYBR gold, ethidium bromide, acridines, proflavine, acridine orange, acriflavine, fluorcoumanin, ellipticine, daunomycin, chloroquine, distamycin D, chromomycin, homidium, mithramycin, ruthenium polypyridyls, anthramycin. For example, a DNA binding dye such as SYBR Green binds all double stranded dsDNA and an increase in fluorescence intensity is measured, thus allowing initial concentrations to be determined. A standard PCR reaction cocktail is prepared as usual, with the addition of fluorescent dsDNA dye and added to a sample. The reaction is then run in a liquid heatblock thermal cycler, and after each cycle, the levels of fluorescence are measured with a camera. The dye fluoresces much more strongly when bound to the dsDNA (i.e. PCR product). Because the amount of the dye intercalated into the double-stranded DNA molecules is typically proportional to the amount of the amplified DNA products, one can conveniently determine the amount of the amplified products by quantifying the fluorescence of the intercalated dye using the optical systems of the present invention or other suitable instrument in the art. When referenced to a standard dilution, the dsDNA concentration in the PCR can be determined. In some embodiments the results obtained for a sequence of interest may be normalized against a stably expressed gene ("housekeeping gene") such as actin, GAPDH, or 18s rRNA.

In an embodiment, any of the methods and systems herein can be used for high resolution melt (HRM) analysis of a sample or set of samples. In other instances, a system can include multiple reference genes to pursue expert analysis.

In various embodiments, labels/dyes are detected by systems or devices of the invention. The term "label" or "dye" refers to any substance which is capable of producing a signal that is detectable by visual or instrumental means. Various labels suitable for use in the present invention include labels which produce signals through either chemical or physical means, such as fluorescent dyes, chromophores, electrochemical moieties, enzymes, radioactive moieties, phosphorescent groups, fluorescent moieties, chemiluminescent moieties, or quantum dots, or more particularly, radiolabels, fluorophore-labels, quantum dot-labels, chromophore-labels, enzyme-labels, affinity ligand-labels, electromagnetic spin labels, heavy atom labels, probes labeled with nanoparticle light scattering labels or other nanoparticles, fluorescein isothiocyanate (FITC), TRITC, rhodamine, tetramethylrhodamine, R-phycoerythrin, Cy-3, Cy-5, Cy-7, Texas Red, Phar-Red, allophycocyanin (APC), probes such as Taqman probes, TaqMan Tamara probes, TaqMan MGB probes or Lion probes (Biotools), fluorescent dyes such as SYBR Green I, SYBR Green II, SYBR gold, CellTracker Green, 7-AAD, ethidium homodimer I, ethidium homodimer II, ethidium homodimer III or ethidium bromide, epitope tags such as the FLAG or HA epitope, and enzyme tags such as alkaline phosphatase, horseradish peroxidase, $I^2$-galactosidase, alkaline phosphatase, β-galactosidase, or acetylcholinesterase and hapten conjugates such as digoxigenin or dinitrophenyl, or members of a binding pair that are capable of forming complexes such as streptavidin/biotin, avidin/biotin or an antigen/antibody complex including, for example, rabbit IgG and anti-rabbit IgG; fluorophores such as umbelliferone, fluorescein, fluorescein isothiocyanate, rhodamine, tetramethyl rhodamine, eosin, green fluorescent protein, erythrosin, coumarin, methyl coumarin, pyrene, malachite green, stilbene, lucifer yellow, Cascade Blue, dichlorotriazinylamine fluorescein, dansyl chloride, phycoerythrin, fluorescent lanthanide complexes such as those including Europium and Terbium, Cy3, Cy5, molecular beacons and fluorescent derivatives thereof, a luminescent material such as luminol; light scattering or plasmon resonant materials such as gold or silver particles or quantum dots; or radioactive material including 14C, 123I, 124I, 125I, 131I, Tc99m, 35S or 3H; or spherical shells, and probes labeled with any other signal generating label known to those of skill in the art. For example, detectable molecules include but are not limited to fluorophores as well as others known in the art as described, for example, in Principles of Fluorescence Spectroscopy, Joseph R. Lakowicz (Editor), Plenum Pub Corp, 2nd edition (July 1999) and the 6th Edition of the Molecular Probes Handbook by Richard P. Hoagland.

Intercalating dyes are detected using the devices of the invention include but are note limited to phenanthridines and acridines (for example, ethidium bromide, propidium iodide, hexidium iodide, dihydroethidium, ethidium homodimer-1 and -2, ethidium monoazide, and ACMA); some minor grove binders such as indoles and imidazoles (for example, Hoechst 33258, Hoechst 33342, Hoechst 34580 and DAPI); and miscellaneous nucleic acid stains such as acridine orange (also capable of intercalating), 7-AAD, actinomycin D, LDS751, and hydroxystilbamidine. All of the aforementioned nucleic acid stains are commercially available from suppliers such as Molecular Probes, Inc.

Still other examples of nucleic acid stains include the following dyes from Molecular Probes: cyanine dyes such as SYTOX Blue, SYTOX Green, SYTOX Orange, POPO-1, POPO-3, YOYO-1, YOYO-3, TOTO-1, TOTO-3, JOJO-1, LOLO-1, BOBO-1, BOBO-3, PO-PRO-1, PO-PRO-3, BO-PRO-1, BO-PRO-3, TO-PRO-1, TO-PRO-3, TO-PRO-5, JO-PRO-1, LO-PRO-1, YO-PRO-1, YO-PRO-3, PicoGreen, OliGreen, RiboGreen, SYBR Gold, SYBR Green I, SYBR Green II, SYBR DX, SYTO-40, -41, -42, -43, -44, -45 (blue), SYTO-13, -16, -24, -21, -23, -12, -11, -20, -22, -15, -14, -25 (green), SYTO-81, -80, -82, -83, -84, -85 (orange), SYTO-64, -17, -59, -61, -62, -60, -63 (red). Other detectable markers include chemiluminescent and chromogenic molecules, optical or electron density markers, etc.

As noted above in certain embodiments, labels comprise semiconductor nanocrystals such as quantum dots (i.e., Qdots), described in U.S. Pat. No. 6,207,392. Qdots are commercially available from Quantum Dot Corporation. The semiconductor nanocrystals useful in the practice of the invention include nanocrystals of Group II-VI semiconductors such as MgS, MgSe, MgTe, CaS, CaSe, CaTe, SrS, SrSe, SrTe, BaS, BaSe, BaTe, ZnS, ZnSe, ZnTe, CdS, CdSe, CdTe, HgS, HgSe, and HgTe as well as mixed compositions thereof; as well as nanocrystals of Group III-V semiconductors such as GaAs, InGaAs, InP, and InAs and mixed compositions thereof. The use of Group IV semiconductors such as germanium or silicon, or the use of organic semiconductors, may also be feasible under certain conditions. The semiconductor nanocrystals may also include alloys comprising two or more semiconductors selected from the group consisting of the above Group III-V compounds, Group II-VI compounds, Group IV elements, and combinations of same.

In addition to various kinds of fluorescent DNA-binding dye, other luminescent labels such as sequence specific probes can be employed in the amplification reaction to facilitate the detection and quantification of the amplified product. Probe based quantitative amplification relies on the sequence-specific detection of a desired amplified product. Unlike the dye-based quantitative methods, it utilizes a luminescent, target-specific probe (for example, TaqMan® probes) resulting in increased specificity and sensitivity. Methods for performing probe-based quantitative amplification are well established in the art and are taught in U.S. Pat. No. 5,210,015.

In another embodiment fluorescent oligonucleotide probes are used to quantify the DNA. Fluorescent oligonucleotides (primers or probes) containing base-linked or terminally-linked fluors and quenchers are well-known in the art. They can be obtained, for example, from Life Technologies (Gaithersburg, Md.), Sigma-Genosys (The Woodlands, Tex.), Genset Corp. (La Jolla, Calif.), or Synthetic Genetics (San Diego, Calif.). Base-linked fluors are incorporated into the oligonucleotides by post-synthesis modification of oligonucleotides that are synthesized with reactive groups linked to bases. One of skill in the art will recognize that a large number of different fluorophores are available, including from commercial sources such as Molecular Probes, Eugene, Oreg. and other fluorophores are known to those of skill in the art. Useful fluorophores include: fluorescein, fluorescein isothiocyanate (FITC), carboxy tetrachloro fluorescein (TET), NHS-fluorescein, 5 and/or 6-carboxy fluorescein (FAM), 5- (or 6-) iodoacetamidofluorescein, 5-{[2(and 3)-5-(Acetylmercapto)-succinyl]amino}fluorescein (SAMSA-fluorescein), and other fluorescein derivatives, rhodamine, Lissamine rhodamine B sulfonyl chloride, Texas red sulfonyl chloride, 5 and/or 6 carboxy rhodamine (ROX) and other rhodamine derivatives, coumarin, 7-amino-methyl-coumarin, 7-Amino-4-methylcoumarin-3-acetic acid (AMCA), and other coumarin derivatives, BODIPY™ fluorophores, Cascade Blue™ fluorophores such as 8-methoxypyrene-1,3, 6-trisulfonic acid trisodium salt, Lucifer yellow fluorophores such as 3,6-Disulfonate-4-amino-naphthalimide, phycobiliproteins derivatives, Alexa fluor dyes (available from Molecular Probes, Eugene, Oreg.) and other fluorophores known to those of skill in the art. For a general listing of useful fluorophores, see also Hermanson, G. T., BIOCONJUGATE TECHNIQUES (Academic Press, San Diego, 1996).

Embodiments using fluorescent reporter probes produce accurate and reliable results. Sequence specific RNA or DNA based probes are used to specifically quantify the probe sequence and not all double stranded DNA. This also allows for multiplexing—assaying for several genes in the same reaction by using specific probes with different-colored labels.

In one embodiment PCR is carried out in a device of the invention configured as a thermal cycler. In an embodiment, the thermal cycler further comprises an optical assembly. In another embodiment the thermal block of the thermal cycler rapidly and uniformly modulates the temperature of samples contained within sample vessels to allow detection of amplification products in real time. In another embodiment the detection is via a non-specific nucleic acid label such as an intercalating dye, wherein the signal index, or the positive fluorescence intensity signal generated by a specific amplification product is at least 3 times the fluorescence intensity generated by a PCR control sample, such as about 3.5, 4.5, 5, 5.5, 6, 6.5, 7, 7.5, 8, 8.5, 9, 9.5, 10, 10.5, or 11. In an embodiment the thermal cycler may modulate the sample temperature by more than 10° C. per second, such as 10.5° C. per second.

In one embodiment an RNA based probe with a fluorescent reporter and a quencher held in adjacent positions is used. The close proximity of the reporter to the quencher prevents its fluorescence; it is only after the breakdown of the probe that the fluorescence is detected. This process depends on the 5' to 3' exonuclease activity of the polymerase used in the PCR reaction cocktail.

Typically, the reaction is prepared as usual, with the addition of the sequence specific labeled probe the reaction commences. After denaturation of the DNA the labeled probe is able to bind to its complementary sequence in the region of interest of the template DNA. When the PCR reaction is heated to the proper extension temperature by the thermal block, the polymerase is activated and DNA extension proceeds. As the polymerization continues it reaches the labeled probe bound to the complementary sequence of DNA. The polymerase breaks the RNA probe into separate nucleotides, and separates the fluorescent reporter from the quencher. This results in an increase in fluorescence as detected by the optical assembly. As PCR progresses more and more of the fluorescent reporter is liberated from its quencher, resulting in a well defined geometric increase in fluorescence. This allows accurate determination of the final, and initial, quantities of DNA.

In various applications, devices of the invention can be utilized for in vitro diagnostic uses, such as detecting infectious or pathogenic agents. In one embodiment, PCR is conducted using a device of the invention to detect various such agents, which can be any pathogen including without any limitation bacteria, yeast, fungi, virus, eukaryotic parasites, etc; infectious agent including influenza virus, parainfluenza virus, adenovirus, rhinovirus, coronavirus, hepatitis viruses A, B, C, D, E, etc, HIV, enterovirus, papillomavirus, coxsackievirus, herpes simplex virus, or Epstein-Barr virus; bacteria including *Mycobacterium, Streptococcus, Salmonella, Shigella, Staphylcococcus, Neisseria, Pseudomonads, Clostridium*, or *E. coli*. It will be apparent to one of skill in the art that the PCR, sequencing reactions and related processes are readily adapted to the devices of the invention for use to detect any infectious agents.

While preferred embodiments of the present invention have been shown and described herein, it will be obvious to those skilled in the art that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A system comprising:
   a thermal assembly configured to hold a sample plate;
   an optical assembly in a fixed position relative to the thermal assembly, the optical assembly comprising:
   a multifaceted mirror having at least three faces that separates excitation and emission beams along separate optical paths;
   at least one array of excitation sources configured to emit excitation energy along an excitation optical path; and
   a detector configured to receive emission energy along a detection optical path, wherein the excitation optical path, multifaceted mirror and detection optical path are in the same plane.

2. The system of claim 1, wherein the system further comprises one or more of an excitation source assembly comprising an array of excitation sources; an emission filter slide; a detection lens assembly; a set of excitation optics; or a control assembly.

3. The system of claim 2, wherein the system comprises two excitation source assemblies, two sets of excitation optics and a detector.

4. The system of claim 3, wherein, in the excitation optical path, an excitation source assembly and a set of excitation optics is positioned on one side of the multifaceted mirror and another excitation source assembly and another set of excitation optics is positioned on the other side of the multifaceted mirror.

5. The system of claim 2, wherein the system comprises an excitation source assembly, wherein the excitation source assembly is positioned in the excitation optical path and wherein the excitation source assembly comprises individual light emitting diodes (LEDs) corresponding to individual wells on the sample plate.

6. The system of claim 5, wherein the excitation source assembly further comprises an LED array comprising the LEDs.

7. The system of claim 6, wherein the excitation source assembly further comprises a lenslet array comprising individual lenslets corresponding to individual LEDs in the LED array.

8. The system of claim 6, wherein the multifaceted mirror is positioned in the excitation optical path to direct excitation energy from individual LEDs to the corresponding wells of the sample plate and is further positioned in the detection optical path to direct emission energy from the sample plate to a detector.

9. The system of claim 2, wherein the system further comprises an emission filter slide comprising at least one emission filter.

10. The system of claim 9, wherein the emission filter slide is positioned in the detection optical path between the multifaceted minor and the detector.

11. The system of claim 10, wherein the emission filter slide comprises four emission filters, each emission filter filtering a different wavelength.

12. The system of claim 11, wherein the system further comprises an emission filter motor for moving the emission filter slide.

13. The system of claim 2, wherein the system comprises a set of excitation optics, the set of excitation optics comprising an excitation filter and two lenses.

14. The system of claim 1, wherein the detector is positioned in the detection optical path and is capable of detecting emission energy from the sample plate.

15. The system of claim 14, wherein the emission energy is fluorescent emission and the fluorescent emission is directed to the detector from the multifaceted mirror.

16. The system of claim 1, wherein the system further comprises a movable lid that is positioned to move around the optical assembly and wherein the movable lid comprises a heated lid configured to mate with the sample plate.

17. The system of claim 1, wherein the thermal assembly comprises a thermal block comprising the sample plate.

18. The system of claim 17, wherein a liquid composition occurs within the thermal block and external to the sample plate.

19. The system of claim 1, further comprising
(a) at least one excitation source assembly positioned in the excitation optical path, wherein the excitation source assembly comprises individual light emitting diodes (LEDs) corresponding to individual wells on the sample plate; and
(b) an emission filter slide positioned in the detection optical path between the multifaceted minor and the detector, wherein the emission filter slide comprises at least one emission filter,
wherein the multifaceted mirror is positioned in the excitation optical path to direct excitation energy from individual LEDs to the corresponding wells of the sample plate and wherein the multifaceted mirror is further positioned in the detection optical path to direct fluorescence emission from the sample plate to the detector.

20. The system of claim 19, wherein the excitation optical path comprises two excitation source assemblies and two sets of excitation optics.

21. The system of claim 20, wherein each set of excitation optics comprises an excitation filter and two lenses.

22. The system of claim 21, wherein each excitation source assembly comprises an LED backplate to which an LED array comprising the LEDs is mounted, a lenslet array comprising individual lenslets corresponding to individual LEDs in the LED array, wherein the lenslet array is positioned to transmit the excitation energy from the LEDs on the LED array to the multifaceted mirror and an excitation source cooling portal positioned to cool the LED backplate.

23. The system of claim 19, wherein the emission filter slide comprises four emission filters, each emission filter filtering a different wavelength.

24. The system of claim 23, wherein the system further comprising an emission filter motor for moving the emission filter slide.

25. The system of claim 19, further comprising at least one detection lens assembly positioned between the emission filter slide and the detector.

26. The system of claim 19, wherein the system further comprises a moveable lid that is positioned to move around the optical assembly and wherein the movable lid comprises a heated lid configured to mate with the sample plate.

27. The system of claim 19, wherein the thermal assembly comprises a thermal block comprising the sample plate.

28. The system of claim 27, wherein a liquid composition occurs within the thermal block and external to the sample plate.

* * * * *